United States Patent [19]
Duer

[11] Patent Number: 5,820,142
[45] Date of Patent: Oct. 13, 1998

[54] SANITARY PROTECTIVE COVERINGS FOR HAND-PROPELLED CART USE

[76] Inventor: Sandra Dee Duer, Rte. 5, Box 5234, East Stroudsburg, Pa. 18301

[21] Appl. No.: 434,009

[22] Filed: May 3, 1995

Related U.S. Application Data

[63] Continuation-in-part of Ser. No. 171,066, Dec. 21, 1993, Pat. No. 5,429,377.
[51] Int. Cl.⁶ ...................................................... B62B 3/02
[52] U.S. Cl. ..................................... 280/33.992; 150/154
[58] Field of Search ..................... 280/33.992, 33.993, 280/DIG. 4, 304.1; 248/251, 252; 4/608, 609

[56] References Cited

U.S. PATENT DOCUMENTS

| | | | |
|---|---|---|---|
| 3,866,649 | 2/1975 | Bringmann | 280/33.992 |
| 4,805,937 | 2/1989 | Boucher et al. | 280/33.992 |
| 4,881,746 | 11/1989 | Andreesen | 280/33.992 |
| 5,215,319 | 6/1993 | Farris | 280/33.992 |
| 5,429,377 | 7/1995 | Duer | 280/33.992 |

*Primary Examiner*—Richard M. Camby
*Attorney, Agent, or Firm*—Charles A. Wilkinson

[57] ABSTRACT

The present invention discloses sanitary coverings for the handles of hand-propelled carts. The coverings may be portable. The coverings may be disposable or recyclable. Various fastening arrangements may be used along the edges of the sanitary coverings to allow the coverings to be securely wrapped about the handles of hand-propelled carts. The preferred arrangement utilizes a partially closed crescent shaped resilient plastic sanitary covering. Various improvements upon the basic tubular sanitary coverings include the use of flaps on the ends thereof to cover larger portions of the surface areas of the handles as well as the sides of carts, and flexible corrugated portions in the structure of the sanitary coverings to accommodate handles and supporting members of various types. The sanitary coverings may also take the form of recyclable, sturdy, resilient, split plastic tubes capable of being dispensed one-at-a-time from dispensers located on the premises of commercial establishments.

12 Claims, 11 Drawing Sheets

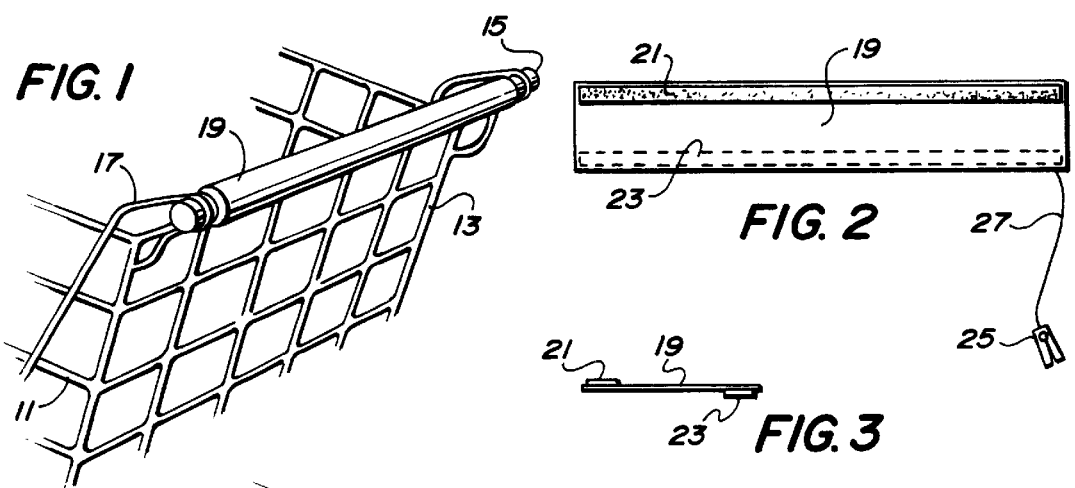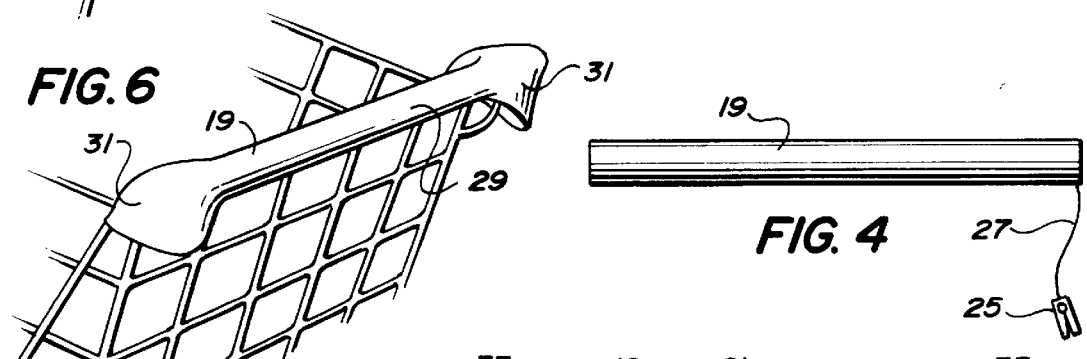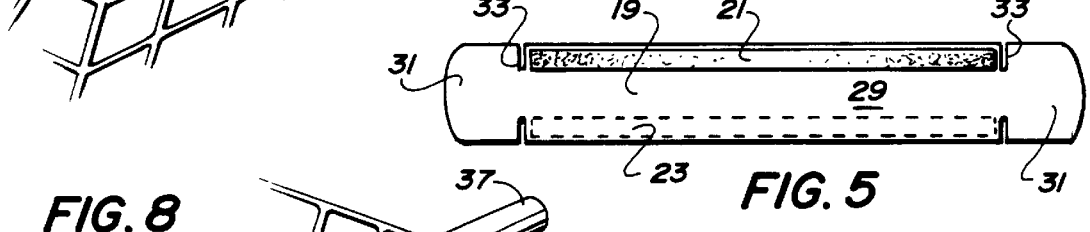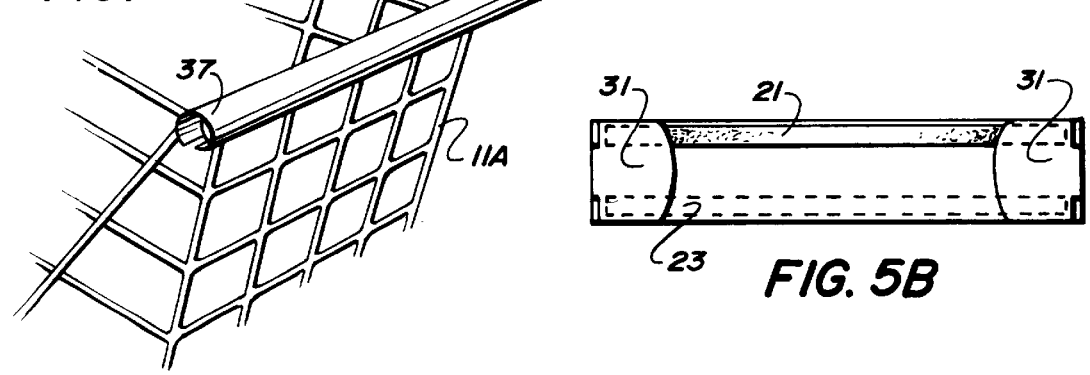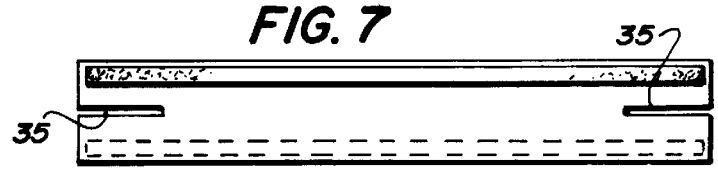

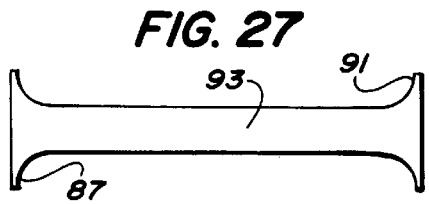
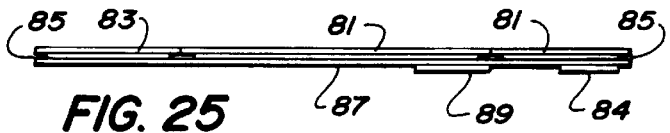
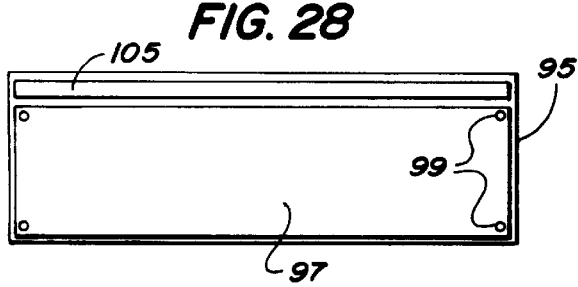
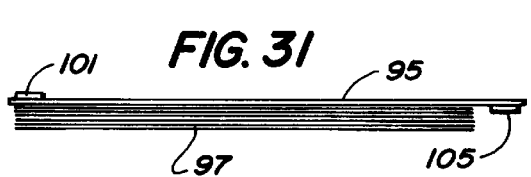
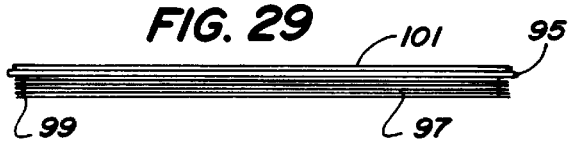
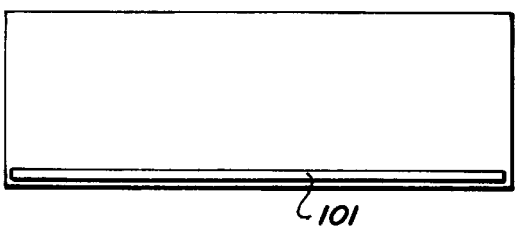
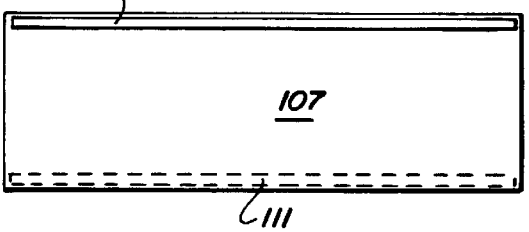

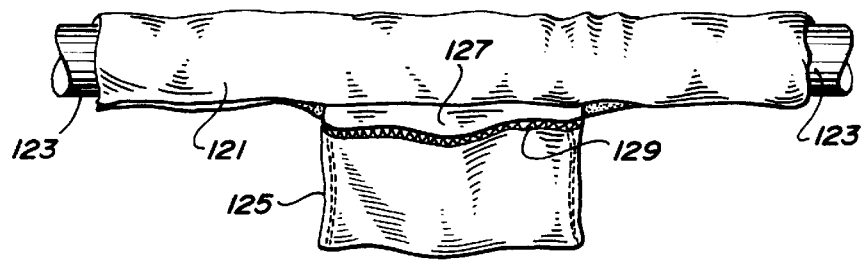
FIG. 38
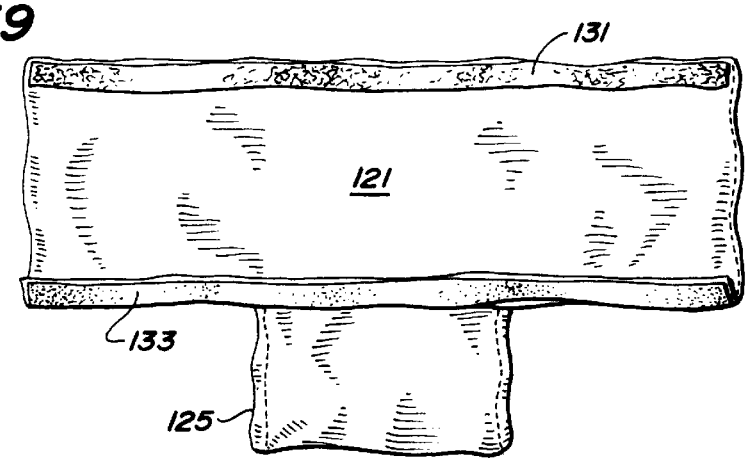
FIG. 39
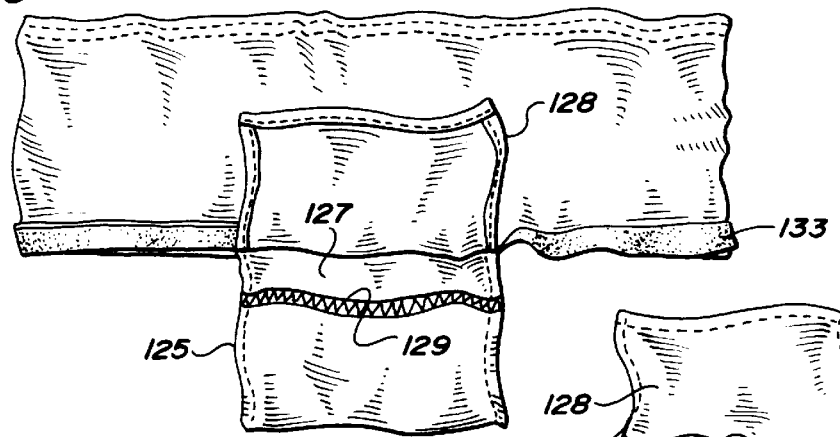
FIG. 40
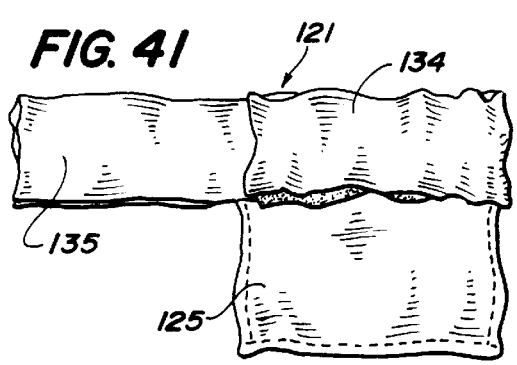
FIG. 41
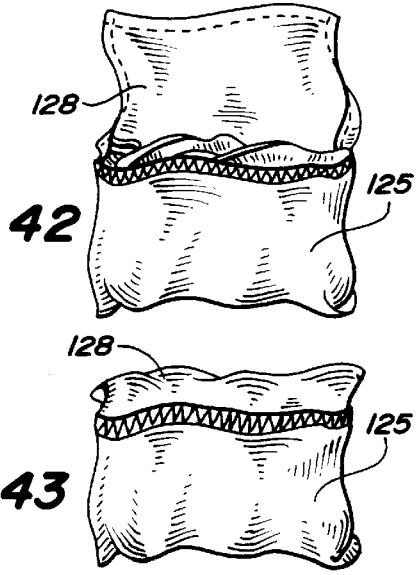
FIG. 42
FIG. 43

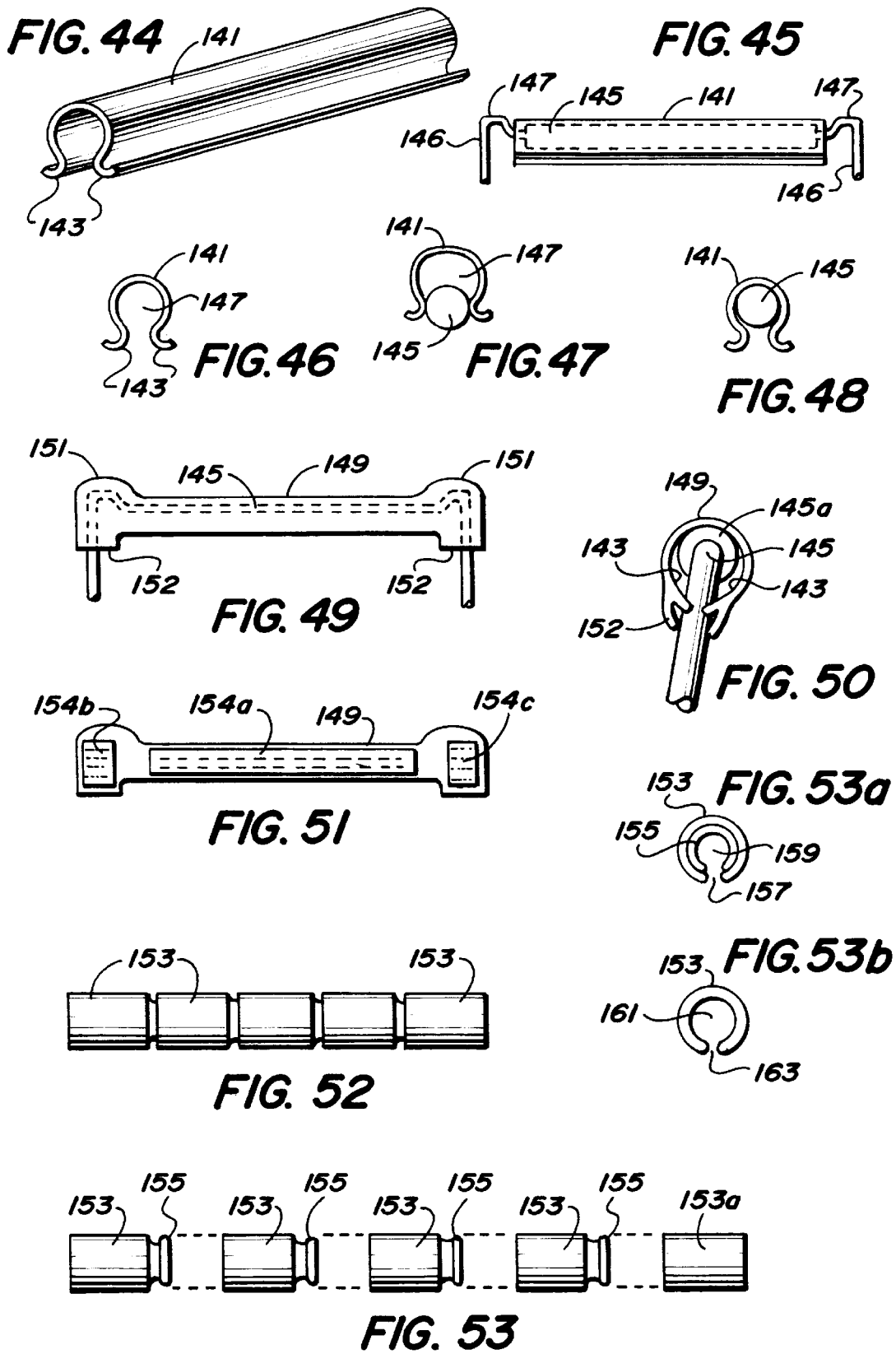

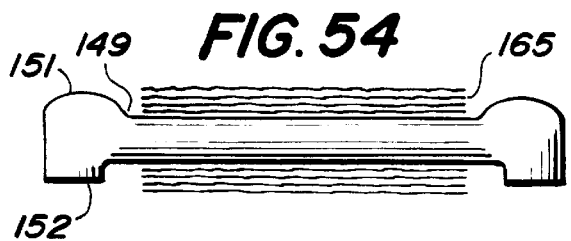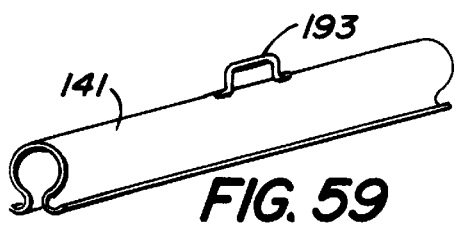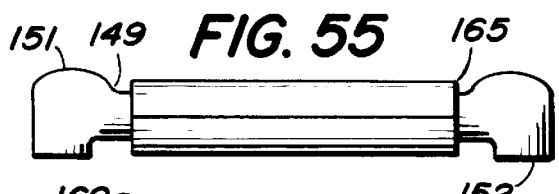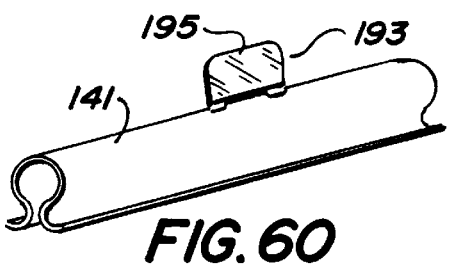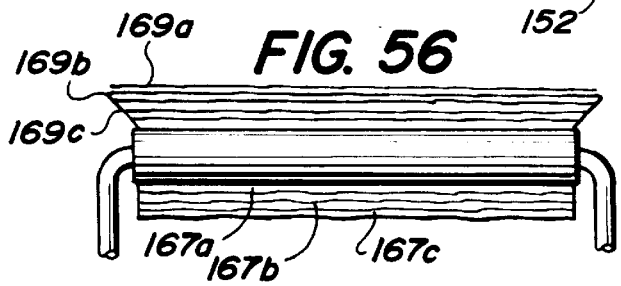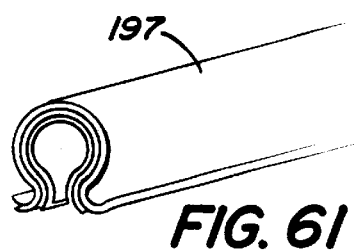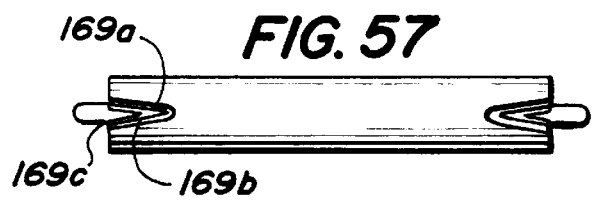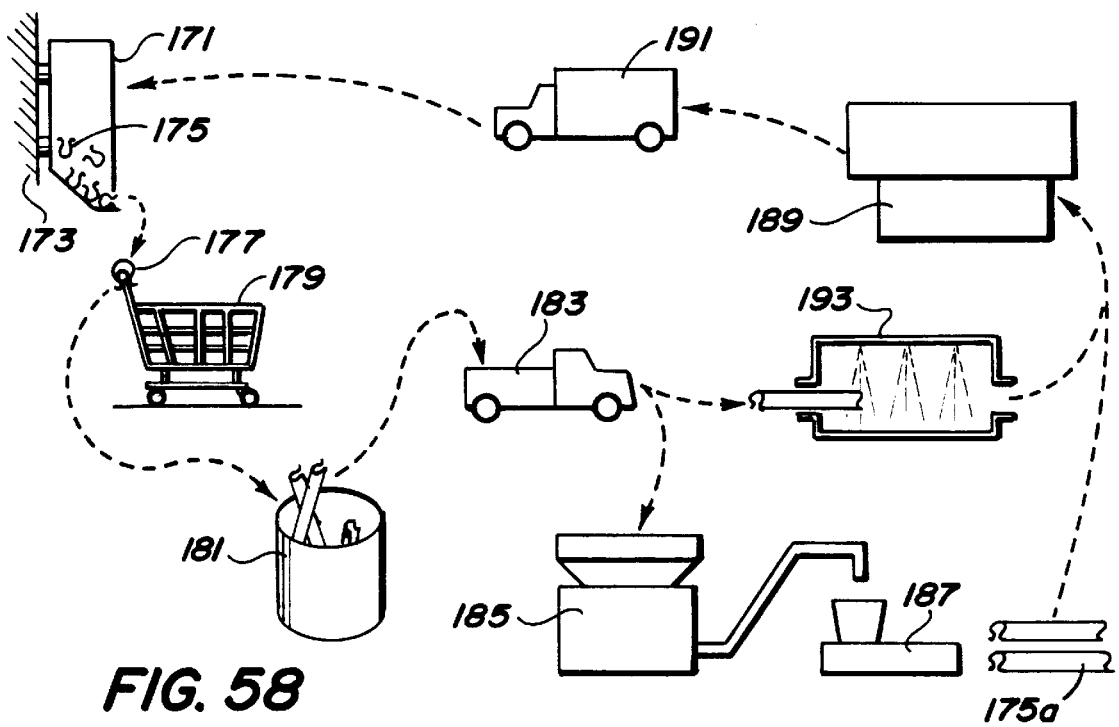

FIG. 64
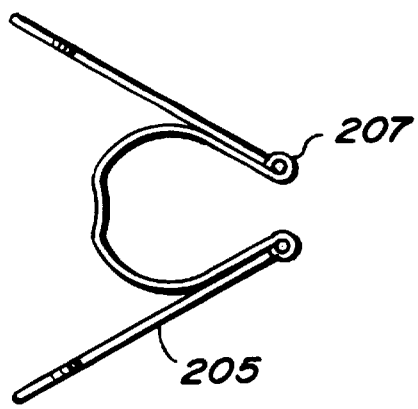
FIG. 62
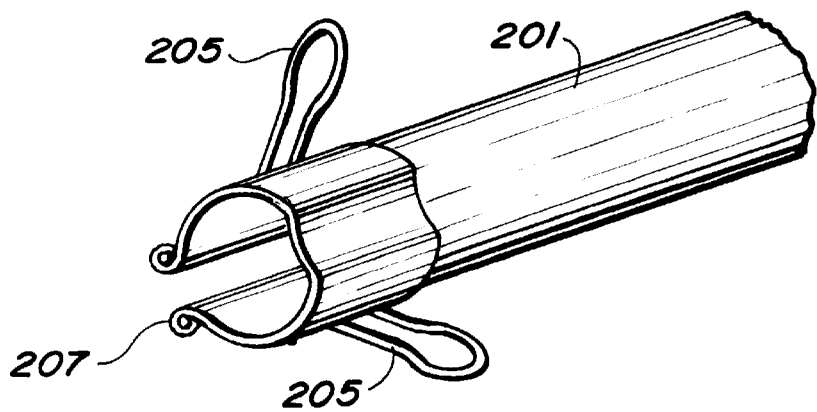
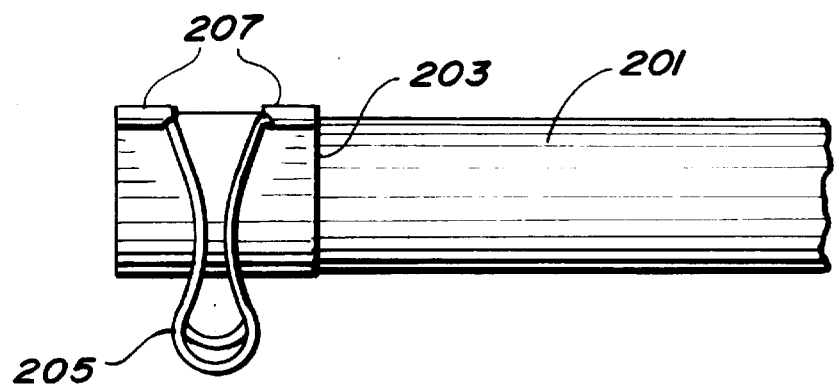
FIG. 63

SANITARY PROTECTIVE COVERINGS FOR HAND-PROPELLED CART USE

RELATED APPLICATIONS

This application is a continuation-in-part of U.S. application Ser. No. 08/171,066, now U.S. Pat. No. 5,429,377, entitled "Sanitary, Protective Covers for Shopping Cart Use" filed Dec. 21, 1993 by the same inventor.

BACKGROUND OF THE INVENTION (1) Field of the Invention

This invention relates, generally, to sanitary coverings, and, more particularly, to sanitary coverings for hand-propelled carts and the like, and, even more particularly, to sanitary coverings for the handles of hand-propelled carts to prevent the passage of infectious agents from one cart handler or user to another as well as to relieve anxiety on the part of users of hand-propelled carts in public places concerning contamination from previous users.

(2) Description of the Prior Art

It is well known that disease agents are passed or vectored from infected individuals to other individuals directly, through body contact, or indirectly, through contact with objects that have come into body contact with infected individuals. While disease agents such as the cold virus typically do not remain infectious outside of the human body for more than a few hours because of drying or desiccation, many similar viruses will remain active outside of the body for up to six hours in moist conditions and up to four hours in dry conditions. There are also many bacterial disease organisms that may be transferred directly or indirectly and that may be infectiously viable for considerably longer periods of time. For example, some strains of staphylococcus and streptococci bacteria are quite resistant to drying and thus remain infectious for long periods of time. Indeed, staphylococcus aureus has achieved considerable notoriety as a so-called nosocomial, or hospital, infectant—one that is frequently spread in hospitals as well as in other environments via objects that come into contact with susceptible individuals.

One prime source of infectious contact is often completely ignored by most persons. This is the handle of the ubiquitous shopping cart found in almost all food stores and supermarkets as well as in other stores such as discount drug stores. Almost everyone eventually ends up intimately grasping the handles of these hand-propelled carts. Such handles are almost never cleaned and are handled by scores of people on a daily basis. Many of these people pay less attention to their personal hygiene than might be desirable. Even fastidiously clean individuals may unwittingly transfer disease organisms to others via the handles of hand-propelled carts. Some members of the public recognize this danger and are loathe to touch the handles of hand-propelled carts. Indeed, parents have begun to recognize that it may be detrimental for their children to chew or teethe on cart handles (not an uncommon occurrence). While some partial coverings have been designed to prevent such chewing or teething directly on the cart handles, none, so far as the Applicant is aware, are suitable for protecting both children and adults. Thus, there has, until now, been little that the average person could do to avoid contact with and contamination from cart handles.

In the past, stores have provided paper or plastic advertising coverings for the handles of their hand-propelled carts. Such advertising coverings worsened rather than improved the problem of preventing transfer of infectious material from one individual to another because of the texture of the coverings and because the coverings were not changed for each new cart user. Indeed, these advertising coverings have been inherently more likely to retain disease organisms than bare cart handles.

Other types of coverings for the handles of hand-propelled carts have also been suggested. For example, U.S. Pat. 4,868,544 discloses a shopping cart handle with a wraparound covering incorporating a radio receiver and/or transmitter for locating and tracking a shopping cart. Again, while such coverings isolate the cart handles from contact with infectious individuals, since they are permanently affixed to the cart handles, they do little, if anything, to prevent the transfer of infectious material from one individual to another and, in fact, they probably increase such transfer because they are formed from materials having rougher textures than typical, original cart handles. Such handles are more likely to retain infectious agents for longer periods in viable states for transfer of disease processes.

There is a need, therefore, for means to prevent transfer of infectious agents from one individual to another via the handles of hand-propelled carts.

OBJECTS OF THE INVENTION

It is an object of the present invention to provide a temporary sanitary covering for the handle of a hand-propelled cart to prevent individuals from transferring disease processes via such handle.

It is also an object of the present invention to provide a readily portable sanitary covering for the handle of a hand-propelled cart.

It is a further object of the present invention to provide a sanitary covering for the handle of a hand-propelled cart that is easy to apply and remove.

It is a still further object of the present invention to provide a temporary disposable sanitary covering for the handle of a hand-propelled cart that can be dispensed at the entrance to a store to those patrons desiring to make use of such covering to protect them from possible contamination from prior customers.

It is a still further object of the present invention to provide a sanitary covering for the handle of a hand-propelled cart that extends over the portions of the cart adjacent to the handle, such as the supports for the handle, to prevent children from grasping such portions of the cart or from touching their mouths to such portions.

It is a still further object of the present invention to provide a sanitary covering for the handle of a hand-propelled cart that effectively covers the handle of a full-sized cart, but that can also be used on mini-sized carts.

It is a still further object of the present invention to provide a sanitary covering for the handle of a hand-propelled cart comprised of a series of disengageable coverings that may be torn off by the customer and placed over the cart handle.

It is a still further object of the present invention to provide a sanitary covering for a hand-propelled cart that may have other useful attachments such as a clip for coupons.

It is a still further object of the present invention to provide a sanitary covering for the handle of a hand-propelled cart that has storage compartments for such things as coupons.

It is a still further object of the present invention to provide a sanitary covering for the handle of a hand-propelled cart that broadly offers means for attaching various desired appendages thereto.

It is a still further object of the present invention to provide a sanitary covering for the handle of a hand-propelled cart that can be dispensed from a roll of such coverings.

It is a still further object of the present invention to provide a sanitary covering for the handle of a hand-propelled cart that has a renewable sanitary surface for contacting the cart handle.

It is a still further object of the present invention to provide a sanitary covering for the handle of a hand-propelled cart that is strong, durable, and completely non-toxic to ensure the safety of children who may place their mouths over such covering.

It is a still further object of the present invention to provide a sanitary covering for the handle of a hand-propelled cart that may be conveniently recycled or sanitized and reused.

Other objects and advantages of the present invention will become evident by careful study of the following descriptions of various embodiments of the invention and the appended drawings.

BRIEF DESCRIPTION OF THE INVENTION

This invention is directed to the protection of the users of hand-propelled carts from possible contamination by disease-inducing organisms or by undesirable filth left by prior users of the carts. As such, the invention comprises a sanitary covering that may be wrapped around the handle of a hand-propelled cart and quickly and easily secured thereto to protect the customer from direct contact with such handle. The preferred arrangement is to have the sanitary covering provided with a Velcro-type attachment along opposite edges to keep the sanitary covering closed. A preferred embodiment is capable of being folded into its own carrying pouch. Such arrangement may be used as a portable, personal sanitary covering.

In another embodiment, a thin paper or plastic covering may be provided with adhesive-type means for securing the edges of the sanitary covering together about the handle. Alternatively, and quite desirably, the covering may be formed from a substantial plastic member that may clip or otherwise lock over a cart handle, that will not be susceptible to damage by a teething or mouthing child, and that may be recycled and/or sanitized between uses. The central sanitary handle covering portion of the invention may have appendages at either end that are provided with a flap-type shield, a shield with flexible folds like the bellows of an accordion, or other extension means for covering portions of the hand-propelled cart adjacent to the handle to prevent accidental contact therewith. Means for preventing the cart user from accidentally moving his/her hand beyond the protected portion of the handle may be provided near the ends of the sanitary covering. A renewable handle covering surface may also be provided within the sanitary covering. Alternatively, a renewable external covering may be provided on a reusable covering or on the cart handle itself or on a replaceable handle to enable the cart user to immediately renew the surface of the cart handle or cart handle shield. Various appendages may be attached to the sanitary handle covering to allow the use of attachments such as coupon holders, calculators, etc. Sanitary coverings may be dispensed from portable, personal dispensers or dispensers provided by a host store.

BRIEF DESCRIPTION OF THE DRAWINGS

FIG. 1 shows a portion of a shopping cart with the sanitary covering of the invention applied to the handle.

FIG. 2 is a plan view of the sanitary covering shown in FIG. 1 in an open position with fastening means on one side shown in full and fastening means on the other side shown in phantom.

FIG. 3 is a side or end view of the sanitary covering depicted in FIG. 2 showing the fastening means applied on opposite sides.

FIG. 4 is a side view of the sanitary covering means of the invention rolled up into tubular form as it is shown in isometric view in FIG. 1.

FIG. 5 is a plan view of an alternative embodiment of the invention in which the sanitary covering has additional end sections made to fold down over both the sides of the handle of the cart and a portion of the cart structure to protect the user of the cart from accidental contact with portions of the cart other than the handle that may be contaminated.

FIG. 5B is a plan view of the embodiment of the invention shown in FIG. 5 partially folded for carrying.

FIG. 6 shows the embodiment of the invention depicted in FIG. 5 applied to the handle of a shopping cart.

FIG. 7 is a plan view of a further embodiment of the invention that is adjustable to fit the handles of carts of different sizes.

FIG. 8 is an isometric view of a portion of the handle of a shopping cart with the embodiment of the invention shown in FIG. 7 secured over the handle and extending to the sides.

FIG. 22 is a side view of a version of an embodiment of the invention having advertising materials on its surface.

FIG. 23 is a plan view of the advertising-type sanitary covering shown in FIG. 22 opened up to reveal the entire top surface.

FIG. 24 is a view of a sanitary covering in which the outside of the covering comprises a series of discount coupons lightly attached to the underlying covering.

FIG. 25 is a side view of the sanitary covering shown in FIG. 24 illustrating how the discount coupons may be perforated to enable them to be removed from the underlying covering.

FIG. 26 shows the sanitary covering arrangements of FIGS. 24 and 25 opened up and spread out to reveal the various coupons that can be accommodated on the surface.

FIG. 27 is a side view of a sanitary covering in which there is a flared section at each side or end that prevents the hands of the cart user from sliding off of the protected area of the cart handle.

FIG. 28 is a bottom or inside view of a portable embodiment of the invention in which a series of disposable coverings are detachably secured to the bottom for disposal after use so that the cart user need not contaminate his/her pocket or purse with the used sanitary covering.

FIG. 29 is a side view of the embodiment depicted in FIG. 28.

FIG. 30 is a top view of the embodiment of the invention shown in FIGS. 28 and 29.

FIG. 31 is an end view of the embodiment of the invention shown in FIGS. 28–30.

FIG. 32 is an end view of the embodiment of the invention shown in FIG. 31 with the sanitary covering wrapped about the handle of a hand-propelled cart.

FIG. 33 is a plan or top view of an embodiment of the invention in which the sanitary covering or shielding may be secured to itself or to the cart handle via magnetic means.

FIG. 38 is a side view of a preferred embodiment of the invention having a dependent pouch extending from one edge of the sanitary covering over a hand-propelled cart handle shown broken away.

FIG. 39 is a side view of the preferred embodiment of the invention shown in FIG. 38 with the sanitary covering opened out preparatory to being secured about the handle of a hand-propelled cart.

FIG. 40 is a side view of an embodiment of the invention similar to that depicted in FIG. 39 showing the opposite side of the sanitary covering.

FIG. 41 is a side view of an embodiment of the invention similar to that depicted in FIG. 38 absent the cart handle and with one end of the sanitary covering folded over preparatory to having the main body portion thereof folded and inserted into the pouch.

FIG. 42 is a side view of the preferred embodiment of the invention depicted in FIGS. 38–40 with the main body portion of the sanitary covering folded and inserted into the pouch with the flap remaining out of the pouch.

FIG. 43 is a side view of the preferred embodiment of the invention depicted in FIG. 42 with the flap tucked into the pouch.

FIG. 44 is an isometric view of an alternative embodiment of the invention wherein the main body portion of the sanitary covering is formed of a sturdy, resilient, plastic material.

FIG. 45 is a side view of the embodiment of the invention depicted in FIG. 44 with the sanitary covering applied to the handle of a hand-propelled cart.

FIG. 46 is an end view or cross-sectional view of the sanitary coverings depicted in FIGS. 44 and 45 preparatory to being applied to the handle of a hand-propelled cart.

FIG. 47 is an end view or cross-sectional view of the embodiment of the invention depicted in FIGS. 44–46 partially expanded as it is pressed over the handle of a hand-propelled cart.

FIG. 48 is an end view or cross-sectional view of the embodiment of the invention depicted in FIGS. 44–47 with the plastic sanitary covering snapped completely over the handle of a hand-propelled cart.

FIG. 49 is a side view, partially in phantom, of an alternative embodiment of the invention shown applied over the handle of a hand-propelled cart.

FIG. 50 is a cross sectional view of one end of the embodiment of the invention shown in FIG. 49.

FIG. 51 is a side view of a sanitary covering, such as depicted in FIG. 49, before it is applied to the handle of a hand-propelled cart showing printed advertising or other material applied to the outside of the covering.

FIG. 52 is a side view of an embodiment of the invention in which the sanitary covering, which is formed of sturdy resilient plastic material as in FIGS. 44–51, is comprised of separate articulated sections that may be conveniently disassembled or re-assembled when not in use or re-assembled over a hand-propelled cart handle.

FIG. 53 is a side view of the individual sections shown in FIG. 52 disassembled from each other.

FIGS. 53A and 53B are end views of the individual sections of the embodiment of the sanitary covering shown in FIG. 52 disassembled and partially separated from each other viewed from opposite ends.

FIG. 54 is a side view in section of an alternative embodiment of the invention in which a sanitary covering shown wrapped about the central section of the handle of a hand-propelled cart is formed of a series of tear sheets that may be removed serially from the handle to provide serially renewed sterile surfaces.

FIG. 55 is a side view of the embodiment of the invention shown in section in FIG. 54.

FIG. 56 is a side-sectional view of an alternative embodiment of the invention depicted in FIGS. 54 and 55 wherein the mass of sheets adhered to each other about the handle of the hand-propelled cart has a slanted undercut at its upper end to facilitate removal of individual sheets after consecutive uses of the cart.

FIG. 57 is a top view of the embodiment of the invention shown in FIG. 56 partially cut away or sectioned to show the gradually increasing slanted central upper sections of the individual sheets that allow sheets to be removed to renew the surfaces of sanitary coverings.

FIG. 58 is a flow diagram of a procedure for recycling sanitary coverings such as those shown in FIGS. 44–48.

FIG. 59 is an isometric view of a sanitary covering as shown in FIGS. 44–48 having a handle to facilitate both placement of the covering over the handle of a hand-propelled cart and removal of the covering therefrom.

FIG. 60 is an isometric view of a sanitary covering with a handle such as shown in FIG. 59 but with the handle covered by a protective shield that may be breached when a new cart user wishes to remove the previous sanitary covering from the cart handle.

FIG. 61 is an isometric view depicting a series of sanitary coverings similar to those shown in FIGS. 44–48 but preferably formed from a somewhat more resilient or flexible material having a more restricted cross-section such that a series of sanitary coverings may be snapped first over the handle of a hand-propelled cart and then consecutively over the already-snapped-on coverings so that the original sanitary covering does not have to be removed before applying subsequent coverings.

FIG. 62 is an isometric view of a sanitary covering with an integral clip for temporarily but firmly securing the covering over the handle of a hand-propelled cart.

FIG. 63 shows the embodiment of the invention depicted in FIG. 62 applied to the handle of a shopping cart.

FIG. 64 is an end view of a sanitary covering shown in FIGS. 62 and 63.

DESCRIPTION OF THE PREFERRED EMBODIMENTS

Figure 9:
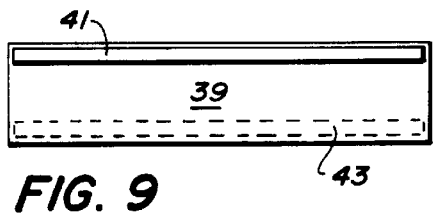
FIG. 9 is an alternative embodiment of the invention in which the sanitary covering is a thin plastic or paper composition having adhesive sections on the surface for securing around a handle.

FIG. 1 is an isometric view of the rear portion of a shopping cart 11 of typical wire mesh construction 13 with a handle 15 extending outwardly and somewhat upwardly from the top of the cart 11. The handle 15 is supported on handle brackets 17 and has a sanitary covering 19 secured about it. It should be appreciated that such sanitary covering has been placed about the handle to protect the cart user's hands from contamination by disease vectors deposited on the surface of the handle by previous users of the cart.

FIG. 2 is a plan view of one side of the sanitary covering 19 shown wrapped about the handle 15 in FIG. 1. FIG. 3 is an end view of the sanitary covering 19 shown wrapped about the handle 15 in FIG. 1. The sanitary covering 19 may be formed from a smooth, preferably water-resistant or waterproof material that may be the material found in outdoor sport clothing. The sanitary covering 19 may contain padding to provide a pleasant feeling grip for the cart user. Such padded sanitary covering 19 is preferably provided with a Velcro or Velcro-type fastener 21 at one side. At the other side, the covering 19 is provided with a comparable Velcro-type fastener 23 as depicted in FIG. 3. The fasteners 21 and 23 are arranged and constructed to be brought together when the sanitary covering 19 is wrapped about the handle 15 and to interlock to firmly secure the sanitary covering about the cart handle. Any self-adherent fastener or adhesive may be used in place of the Velcro-type fastener. However, there are few self-adherents as convenient and effective as Velcro-type adherents. The Velcro-type fasteners 21 and 23 depicted in FIG. 3 are on opposite sides of the sanitary covering 19 so that the covering may be easily formed into a cylinder secured to itself. The Velcro-type fasteners 21 and 23 may also be arranged on the same side of the sanitary covering 19 so that when the covering is placed about the handle 15, the one side will be looped under or against the other side to enable the Velcro-type fasteners to meet.

FIG. 4 is a side view of the sanitary covering 19 secured into a tubular arrangement as though it were wrapped about the handle 15 of a hand-propelled cart. The sanitary covering 19 as shown in FIG. 4 is provided with a clip 25 secured on a thong 27 and adapted to secure store coupons, sales literature, and the like to the cart within easy reach of the cart user.

Since the sanitary covering is also intended to protect children who teethe or chew on cart handles from contamination by disease organisms, it is highly desirable, if not critical, to form at least the exterior of the sanitary covering from a "child-proof" material. There are several such materials that have been approved by testing laboratories and government agencies. A preferred material in No. 6200 Oxford polyamide plastic with a ¾ ounce polyurethane coating. The base of this material is formed from DuPont 6.6 nylon with a ¾ ounce per square unit polyurethane coating and meets FisherPrice Standard Specifications for toy materials. This non-toxic material is practically indestructible when it comes to abuse by children. It is also smooth and nonporous and, hence, is not easily contaminated. One may purchase this material from Rockville Fabric Corporation located at 22 West 34th Street, New York, N.Y. 10001.

FIG. 5 shows an improved embodiment of the invention in which the main portion 29 of the sanitary covering 19 is provided on the ends with two cowls or flaps 31. When the sanitary covering 19 is coiled about the handle 15, the cowls or flaps 31, when properly disposed, extend over, fall down over, or depend downwardly over the side portions of the handle of the cart 11 shielding the hands of the cart user from such side portions. FIG. 6 shows the embodiment of the invention depicted in FIG. 5 placed over the handle of a shopping cart with the flaps 31 extending over the ends of the handle as well as the ends of the cart. The cowls or flaps 31 are preferably not padded so that they fall easily over the sides of the cart and readily conform to the shape of the ends of the cart handles. Omission of padding on the flaps 31 allows them to be easily wrapped about the exterior of the sanitary covering 19 or, alternatively, folded inside the sanitary covering when it is being carried. Folding the flaps 31 into the interior of the sanitary covering with their cart contact surfaces against the inside of the covering, as shown in FIG. 5B, prevents the outside surfaces of both the sanitary covering and the flaps from coming into contact with each other and causing contamination. Folding the flaps 31 may also cause them to contact the surface of the Velcro-type fasteners 21 and 23, if the fasteners run the length of the main portion 29 of the sanitary covering 19, preventing the fasteners from interlocking when the covering is placed into tubular form for storage, as shown in FIG. 4. Such folding, however, has no detrimental effect since the Velcro-type fasteners are not required to hold the sanitary covering in tubular form when the covering is not being used. The entire sanitary covering 19, particularly the embodiment of FIG. 5, may be formed from a single piece of material that has a tubular portion in the center to which the flaps 31 are attached only at their centers. The separation between the flaps 31 and the main portion 29, as shown in FIG. 5, may be formed by grooves, notches, or channels 33 to facilitate bending and draping the flaps over the sides of the cart handle.

FIG. 7 shows a plan view of an alternative embodiment of the invention in which a longitudinal groove, notch, or channel 35 at each end of the sanitary covering 19 provides a separation through which a handle bracket 17 of a hand-propelled cart handle may extend if the covering in its tubular configuration is too wide or too long for the cart handle. This allows the embodiment of the invention shown in FIG. 7 to be adapted for use not only with the normal size, wide shopping carts found in large markets, but also with the smaller, miniature-type carts found in mass market drug stores, convenience stores, and other establishments where customers are not expected to buy many items at any given time. When the sanitary covering is used on a smaller cart, the groove 35 allows the ends of the covering to extend outwardly over the ends of the cart handle while maintaining the covering's tubular configuration. Any extension of the ends of the covering from the sides of the cart is of no concern, since the covering is flexible and will not damage anything that it touches. The extension of the ends 37 of the sanitary covering 19 over the ends of the cart handle 15 (not shown) is illustrated in FIG. 8 which depicts a narrower cart 11A of the type used in large drug stores and convenience stores. In FIG. 8, the sanitary covering extends only to the ends of the cart handle. However, depending upon the relative widths of the cart and the sanitary covering, the covering may extend beyond the ends of the handle.

Figure 10:
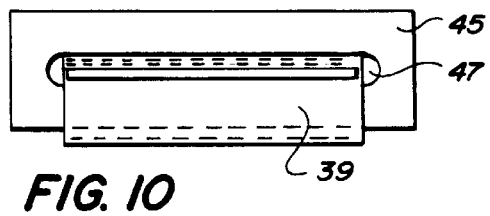
FIG. 10 is a front view of a dispenser for disposable sanitary coverings such as shown in FIG. 9 with one of the coverings extending from a dispensing opening in such dispenser.

FIG. 9 shows a plan view of a disposable sanitary covering 39 having an adhesive material 41 along one edge on one side thereof and preferably a roughened area 43 on the opposite side along the opposite edge of the covering which allows the adhesive material to adhere strongly to the roughened area when the two edges of the covering are brought together. It should be understood, however, that although a roughened area 43 is preferred and is shown, in a simpler embodiment only the adhesive area 41 need be used, provided that the entire sanitary covering is made from a material to which the adhesive will adhere. Alternatively, both areas 41 and 43 could constitute adhesive areas. Preferably, the disposable sanitary covering 39 may be arranged along with other similar coverings to be dispensed from a container 45 like the one depicted in FIG. 10. FIG. 10 shows a box having an elongated orifice or dispensing opening 47 with one of the disposable sanitary coverings 39 extending therefrom. The arrangement is somewhat like a tissue dispenser. However, since the disposable sanitary covering 39 is provided with an adhesive on one side to facilitate its attachment about the handle of a hand-propelled cart, it is preferable that the various disposable sanitary coverings contained in the box 45 be temporarily adhered, one to the other, and folded into alternating sheets so that each sheet may be pulled from the dispenser and progressively detached from the next sheet. Alternatively, the sanitary coverings may be dispensed from a roll of adhered sheets with or without a dispensing box 45.

Figure 11:
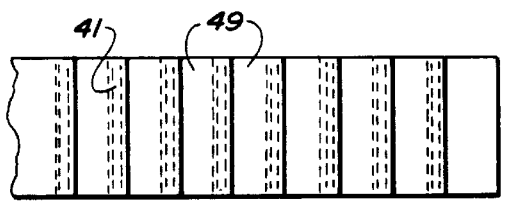
FIG. 11 is a plan view of a series of the disposable strips as shown in FIG. 9 temporarily secured to each other to allow them to be drawn one-by-one from the dispenser 10.
Figure 12:
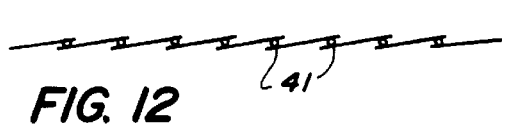
FIG. 12 is a side view of the strips of material depicted in FIG. 11 showing how the strips are overlapped.

FIGS. 11 and 12 show a bottom view and a side view, respectively, of a series of the sanitary coverings depicted in FIG. 9 adhered one to another. The sanitary coverings 39 shown in FIGS. 11 and 12, however, do not include the roughened area 43, since it is assumed that the adhesive 41 is sufficiently adherent to the plain surface of each sheet to hold the sheets together until sufficient lateral shearing strain is applied to progressively break the adhesion of the glue strip and remove the outermost accessible sanitary covering from the underlying sanitary coverings. The inter-adhered collection of sanitary coverings forms a composite strip 49. The glue strips 41 are shown in phantom in FIG. 11 since, with the disposable sanitary coverings attached to each other, the glue always appears between the two sheets, as shown in FIG. 12. It should be appreciated that the individual sheets 39 will be withdrawn from a dispenser such as the box 45 in a manner such that the edges of the sheets are not likely to become snagged on the edge of the opening 47. It should also be appreciated that when an individual sanitary covering has been detached from the adjacent coverings, it may then be easily wrapped about the handle of a hand-propelled cart such as shown in FIGS. 1, 6, or 8.

Figure 12A:
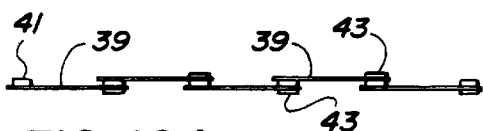
FIG. 12A is a side view of an alternative arrangement for securing the individual sheets together in overlapped fashion with fewer adhesions between adjoining sheets in the dispensing container than between the two sides of the same sheet in actual use.

FIG. 12A shows a side or edge view of an alternative arrangement for connecting the individual sheets together for dispensing in which each individual sheet has the roughened or other surface 43 on the side near the edge opposite the side on which the adhesive is deposited, as shown in FIG. 9. Such sheets are then arranged in a composite strip, as shown in FIG. 12A, with the adhesive sides alternating upwardly and downwardly so that the adhesive of each sheet is secured to a smooth section of the sheet adjacent thereto. In covering a sheet about the handle of a hand-propelled cart, the adhesive end of the sheet is secured with the adhesive opposed to the roughened portion thereof. It should be appreciated that other arrangements are also possible.

Figure 13:
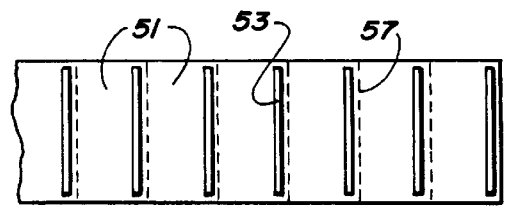
FIG. 13 is a bottom plan view of an alternative arrangement of the invention in which the sanitary covering is provided in a strip that has been perforated so that individual coverings may be torn off and used as a covering about the handle of a hand-propelled cart.

FIG. 13 is a plan view of an alternative form of connected strips of disposable sanitary coverings 51 in which each individual covering is connected to an adjacent covering by a perforated arrangement similar to that of a roll of stamps. In order to prevent the adhesive material 53 from adhering to the dispenser or to undesignated sheets, a backing or tear strip 55 is provided in the embodiment of the invention shown in FIGS. 13 and 14. Such tear strip may be seen in FIG. 14 which shows a side view of the alternative connected strip of sanitary coverings. The perforations 57 are adjacent to adjoining adhesive strips or sections.

Figure 15:
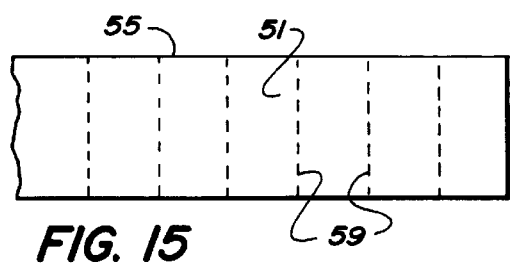
FIG. 15 is a top plan view of the sanitary coverings shown in FIGS. 13 and 14.

FIG. 15 is a bottom view of the tear strip 55 adhered lightly to the bottom of the disposable sanitary covering 51.

Figure 16:
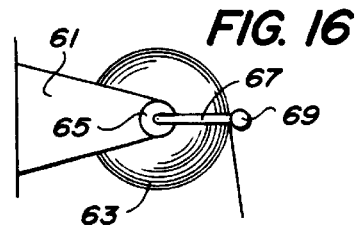
FIG. 16 is a side view of a roll arrangement for dispensing the sanitary coverings depicted in FIGS. 13–15.
Figure 14:
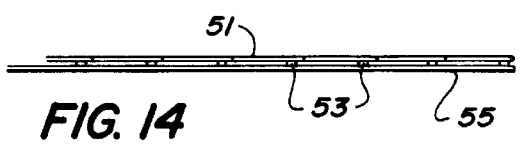
FIG. 14 is a side view of the embodiment of the invention depicted in FIG. 13 showing a tear strip upon the surface to protect adhesive portions that are used on only one side of the sheet.

The tear strip 55 is also provided with perforations 59 similar to the perforations 57 separating individual sheets of the disposable sanitary covering 51. The perforations 59 in the tear strip and the perforations 57 in the strip of disposable sanitary coverings 51 are opposite or adjacent to each other so that one of the sanitary coverings may easily be torn away, the tear strip removed, and the individual covering placed about the handle of a hand-propelled cart with the two edges adhered by means of the adhesive layer 53 between them, such adhesive layer, as shown in FIG. 13, being found on only one side and at one end of each perforated strip of sanitary disposable covering. The embodiment of the invention shown in FIGS. 13–15 is particularly convenient for dispensing from a continuous roll of disposable sanitary coverings. Such a roll, affixed to a horizontal surface (not shown) by a bracket 61, is shown in side view in FIG. 16. A roll of a series of disposable sanitary coverings 51 as shown in FIGS. 13–15 are rotatably journaled upon a small roller 65 provided in the bracket 61, as shown in FIG. 16. It should be appreciated that the composite strip 63 on the roll 65 is the composite strip illustrated in FIGS. 13–15. other suitable strips of severable or otherwise detachable sanitary coverings may be used. While a full tear strip 55 is preferable, it should be appreciated that short, individual tear strips could be used over only the adhesive sections on the faces of the sanitary coverings. The small roll 65 is freely rotatable in the bracket 61. An elongated bracket 67 preferably supports a small guide roll 69 under which the composite strip 63 may be fed. Individual perforated disposable sanitary coverings 51 may be detached therefrom by tearing along the edge of the guide roll 69.

Figure 17:
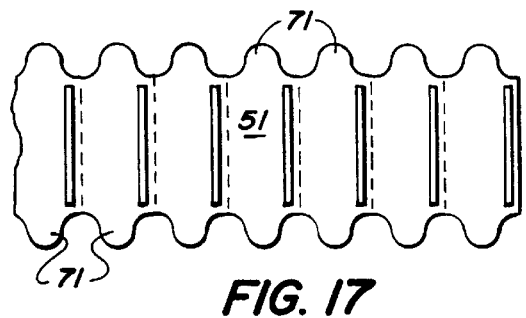
FIG. 17 is a plan view of an alternative arrangement of the invention, similar to that depicted in FIGS. 13–15, in which the sides of the disposable sanitary coverings for the handles of hand-propelled carts are scalloped to provide protective flaps. The extensions on both sides provide flap covering for the sides of the cart as shown in FIGS. 5 and 6.

FIG. 17 shows an alternative version of the invention similar to the perforated tear strip arrangement depicted in FIGS. 13–15. In the alternative version, each of the individual disposable sanitary coverings 51 is provided with two flaps 71. When a sanitary covering is rolled about the handle of a hand-propelled cart, the flaps 71 may depend from the sides of the rolled covering masking outboard portions of the cart and the cart handle preventing a customer's hands from accidentally contacting such cart portions.

Figure 18:
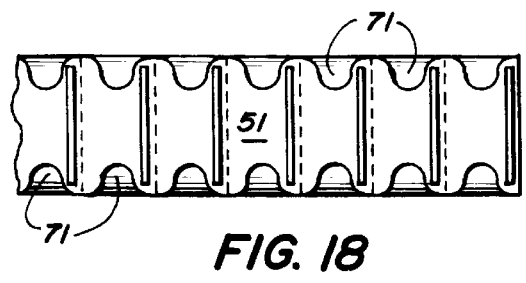
FIG. 18 shows a further embodiment of the sanitary coverings of the invention in which the flaps on the sides are overlapped with the strips to ease dispensing and in which the flaps open up after the sanitary covering is wrapped about the handle.

FIG. 18 shows an arrangement similar to that depicted in FIG. 17 in which the flaps 71 have been folded inwardly to lie against the back of the connected strip of sanitary coverings. This is convenient for dispensing an individual sanitary covering from a roll or other dispenser after which the flaps 71 may be straightened so that, when the covering is detached and wrapped about a cart handle as in FIG. 6, the flaps will depend from the ends of the covering as shown if FIG. 6.

Figure 19:
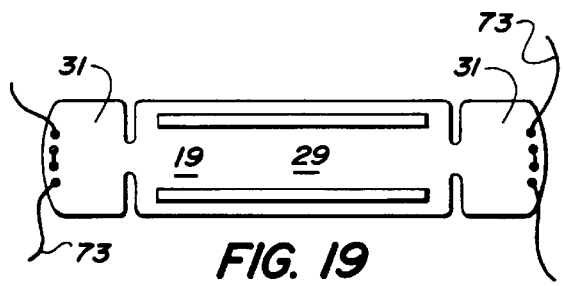
FIG. 19 is a plan view of an alternative embodiment of the invention similar to the embodiment depicted in FIGS. 5 and 6 in which there is provided a further tying means for securing the flaps on the sides of the sanitary covering down against the cart structure.

FIG. 19 is a plan view of an alternative arrangement similar to that shown in FIG. 5 except that there are tie thongs 73 provided on the ends of the flaps 31 so that the flaps can be tied down on the structure of a hand-propelled cart.

Figure 20:
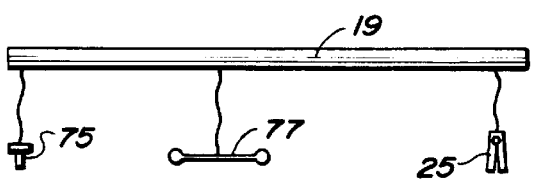
FIG. 20 is a side view of an embodiment of the invention in which various amusements for young children are provided on tethers connected to the side of the sanitary covering.

FIG. 20 shows an individual sanitary covering 19 such as shown in FIG. 4 additionally provided with baby toys and the like, including a pacifier 75 and a rattle 77. A clip 25 is also provided upon the sanitary covering 19.

Figure 21:
FIG. 21 is a side view of the sanitary covering with a calculator attached thereto.

FIG. 21 shows an embodiment of the invention in which a sanitary covering 19, depicted in rolled storage form, is provided with a small calculator 79.

FIG. 22 shows a sanitary covering 51, such as in FIGS. 11–15, having advertising material upon its surface. It should be appreciated that the sanitary covering dispensed from a roll or other dispenser on the premises of a store may be provided with advertising material printed on its surface.

FIG. 23 is a plan view of the outer surface of the individual sanitary covering shown in FIG. 22 opened up to reveal other advertising material.

FIG. 24 shows a variation of the invention in which the surface of the sanitary covering comprises a series of store-type coupons which may have perforated sections between them to facilitate their removal.

FIG. 25 is a side view of the sanitary covering shown in FIG. 24. Individual portions 81 of top sheet 83 secured by adhesive layers 85 to a bottom sheet 87 are removable from such bottom sheet to form individual coupons. The bottom sheet 87 is, in turn, provided with adhesive layers 89 which secure it to the handle of a hand-propelled cart. The sanitary covering shown in FIGS. 24, 25, and 26, therefore, is a composite covering having a bottom sheet 87 that serves as the actual sanitary covering and a top sheet 83 which may be separated into individual coupon portions 81. The top sheet 83 may be detached from the bottom sheet 87 to provide access to the individual coupons 81 which are, in turn, detachable. The glue between the coupons and the sanitary covering is merely a temporary adhesive that serves only to keep the coupons wrapped about the individual sanitary covering until it is desired to redeem them.

FIG. 27 shows a form of sanitary covering such as depicted in FIGS. 1, 4, 6, 20, and 21 in which the ends 91 of the covering 93 are built up to prevent a cart user's hand from straying beyond them. The upturned ends 91 can be formed or shaped by various constructions, including the use of extra padding, molded ends, or inflatable ends.

Figure 34:
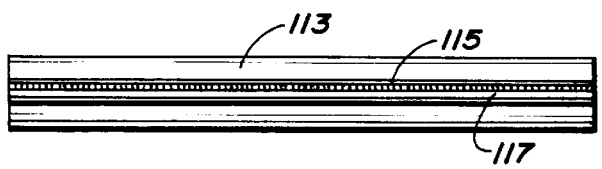
FIG. 34 is a side view of an embodiment of the invention in which the securing means is on the same side of the sanitary covering shown wrapped about the handle of a hand-propelled cart.

FIG. 28 is a bottom view of a particularly desirable portable embodiment of the invention in which the inside or bottom surface of the sanitary covering 95 is provided with its own disposable secondary sanitary covering 97 which, after being used on the handle of a hand-propelled cart, can be removed from the sanitary covering and thrown away with whatever contamination such covering may have accumulated while on the cart handle. FIG. 29 is a side view of the sanitary covering 95 including a series of layers of secondary sanitary coverings 97. As shown in FIG. 28, the coverings 97 are lightly tacked to the sanitary covering 95 using glue impregnations 99 at the corners of the coverings. FIG. 30 is a top view of the sanitary covering 95 depicted in FIGS. 28 and 29 showing an upper adhesive or Velcro-type strip 101. When the sanitary covering 95, shown from the end in FIG. 34, is wrapped about a handle 103, as shown in FIG. 32, the upper adhesive strip 101 allows the secondary sanitary coverings 97, comprised of thin paper tissue or the like, to be completely wrapped about the handle while remaining free to contact another adhesive strip 105 to hold the sanitary covering in place. When the sanitary covering 95 is then removed from the handle 103, the top secondary sanitary covering can be stripped from the bottom and disposed of. The sanitary covering 95 can then be carried in a pocket, a purse, a shopping bag, or the like without risk of contamination.

FIG. 33 is a plan view of a sanitary covering 107 provided on opposite sides with magnetic strips 109 and 111 for adherent interaction or attraction with each other to hold the sanitary covering about the handle of a hand-propelled cart.

Figure 35:
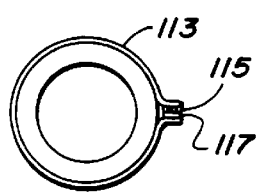
FIG. 35 is an end view of the embodiment of the invention shown in FIG. 34.
Figure 36:
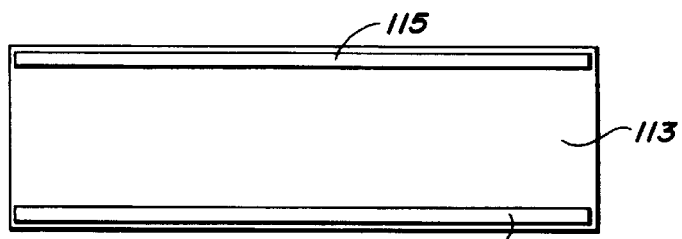
FIG. 36 is an opened-out plan or top view of the embodiment of the invention shown in FIGS. 34 and 35.

FIG. 34 is a side view of an embodiment of the invention in which the adhesive strips or the Velcro-type fasteners of the sanitary covering 113 are disposed upon the same side of the covering and in which 115 and 117 are the Velcro-type fasteners or adhesive strips. FIG. 35 is an end view of the sanitary covering of FIG. 34. FIG. 36 is a plan view of the sanitary covering of FIGS. 34 and 35 opened up. The arrangement shown has the advantage of being easier to apply to the cart handle without contacting either the interior of the covering or the handle surface.

Figure 37:
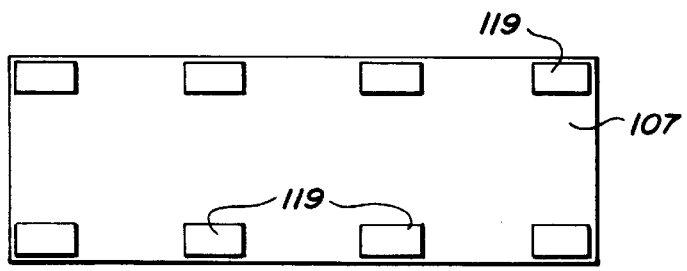
FIG. 37 is a plan view of an embodiment of the invention using magnetic means to secure the sanitary covering directly to the handle of a hand-propelled cart.

FIG. 37 is a plan view of an embodiment of the invention such as shown in FIG. 33 where a series of individual magnets 119 are used instead of elongated magnetic strips 109 and 111 shown in FIG. 33 to hold the sanitary covering 107 together about the handle of a hand-propelled cart. Since a magnetic field will pierce non-magnetic or non-metallic materials, it may be satisfactory to have the magnets 119 or even the magnetic strips 109 and 111 on the same side of the sanitary covering 107 or, alternatively, they may be mounted inside a fabric sanitary covering.

In the above disclosure of sanitary coverings adapted to be dispensed from dispensers of various configurations, the coverings usually comprise single sheets of material such as paper or plastic having sufficient thickness and durability to offer complete temporary protection from contact with the handles of hand-propelled carts and having sufficient flexibility and resiliency to allow them to be easily and conveniently secured about such cart handles. The sheets may be single-layer sheets or composite-layer sheets of plastic or paper coated with smooth, biologically impervious plastic or other surface coatings. Such sheets are at least temporarily childproof. Such sheets are also non-toxic.

FIG. 38 shows a preferred embodiment of the invention for carrying in a cart user's purse or pocket in which a main body portion 121 of the sanitary covering is shown wrapped about a section of cart handle 123, shown cut off at the ends. The main body portion 121 has a pouch 125 attached to one side. The pouch 125 comprises an extension folded over and secured together into a pocket 127 having an upper edge 129.

FIG. 39 shows the main body portion, as described above, opened up just prior to being applied to the handle 123 of a hand-propelled cart. In FIG. 39, the preferred Velcro-type fasteners 131 and 133 are shown on both sides or edges of the main body portion 121 of the sanitary covering. This is the preferable arrangement in the embodiment of the invention incorporating the pouch, as it allows the pouch to depend naturally from one side of the secured-together main body portion. However, the Velcro-type fasteners or adhesive strips may be provided on opposite sides of the main body portion, as shown in FIG. 40. FIG. 40 also shows an additional flap 128 which forms a closure for the pocket 127 when the sanitary covering is wrapped about a cart handle. It is necessary and desirable for the pouch to be sewn or otherwise attached to the main body portion at the top of the Velcro-type fastener or adhesive strip 133 so that such edge can be folded over during use and the entire length attached to the upper strip rather than being partially covered by the pouch. Functionally, this amounts to the same thing as having both strips on the same side, but is more convenient to form or manufacture because the pouch material can be laid upon the main body portion preparatory to sewing the parts together with the Velcro-type fastener laid over the pouch and several sewing passes made to secure the several parts together. On the other hand, if the pouch material is sewn to the main body portion with such material laid so that it extends from one side, it is more difficult to maintain the two in alignment during sewing.

In FIG. 41, the preferred embodiment of the invention as depicted in FIGS. 38 and 39 is shown in a side view similar to that of FIG. 39 with the main body portion 121 secured together as shown in FIG. 38, except that the short section of the handle 123 does not extend through the main body portion, but, instead, one arm 134 of the sanitary covering is folded over into the center while the other arm 135 continues to extend to the side. The flap 128 is hidden by the folded arm 134.

In FIG. 42, the embodiment of the invention depicted in FIG. 41 as well as in FIGS. 38 and 39 is shown with both of the arms 134 and 135 folded inwardly as partially shown in FIG. 41 and then in FIG. 43 with the entire upper section of the sanitary covering 121 folded inwardly into the pocket 127, leaving only a small upper portion of the sanitary covering 121 as a whole extending from the pocket together with the flap 128. The flap 128 may then be folded into the pouch 125 as shown in FIG. 43. In FIG. 43, the folded sanitary covering is compact and all possible contaminated surfaces are retained completely inside of the covering so that the covering can be conveniently inserted into and carried in a purse or pocket. To use the covering, one would merely remove it from the purse or pocket, open it out completely, as shown in FIGS. 39 and 40, and then attach the main body portion 121 about the handle of a hand-propelled cart, as shown in FIG. 38. As an added refinement, the disposable inside protective covering shown in FIGS. 28–31 could also be used within the main body portion 121 of the sanitary covering shown in FIGS. 38–43, however, this is not necessary for making cart users feel completely safe from contamination.

The extending flaps 31 shown in FIGS. 5, 5B, and 6 can also be easily incorporated onto the ends of the main body portion 121 of the sanitary covering shown in FIGS. 38–43 for extending over and shielding the sides of cart handles. Such flaps can then be folded, as shown in FIG. 5B, and inserted, together with the main body portion 121, into the pouch 125, as shown in FIG. 43.

As in the embodiment of the invention depicted in FIG. 2, the embodiment shown in FIGS. 38–43 is preferably closed about a cart handle with a Velcro-type fastener, but it could also be closed by any other suitable self-adherent fastener or temporary adhesive of equivalent strength.

FIG. 44 shows an isometric view of another preferred embodiment of the invention particularly for on-site dispensing by stores. The embodiment of the invention shown in FIG. 44 comprises an elongated plastic member 141 having a hollow interior 147, an essentially horseshoe-shaped cross-sectional profile with a terminal pair of outwardly inclined lips 143, and a length substantially coincident with the length of the straight portion of a hand-propelled cart handle. The plastic member 141 is resilient so that when the outwardly inclined lips 143 are applied against the handle of a hand-propelled cart, the lips will tend to ride on the rounded surface thereof and be forced apart until the handle passes into the hollow interior 147 of the plastic member and the lips snap together again, as shown in FIGS. 45 and 48.

FIG. 45 shows a sanitary covering such as depicted in FIG. 44 applied to the handle 145 of a hand-propelled cart, as shown partially in phantom. Supports 146 for the handle 145 extend from the ends of the plastic member 141. In this embodiment, the handle 145 turns upwardly into an upwardly extending curved portion and then passes downwardly to connect with the main portion of the hand-propelled cart (not shown).

FIG. 46 is an end view or cross-sectional view of the sanitary covering 141 as depicted in FIG. 44. The slightly inclined angle of the outwardly inclined lips 143 is shown as well as the hollow 147 within the resilient plastic member.

FIG. 47 is a cross-sectional view of the resilient plastic member 141 partially forced over a section of a cart handle 145. FIG. 47 shows how the inside surfaces of the outwardly inclined lips slide across the curved surface of a cart handle 145 and urge apart the sides of the plastic member 141.

FIG. 48 is a cross-sectional view of the main body portion of the elongated resilient plastic sanitary covering 141 completely snapped over the handle 145 of a hand-propelled cart. The handle 145 is accommodated in the hollow interior 147 of the plastic member 141. Here, the handle 145 fills only a part of the hollow interior 147 of the sanitary covering 141. It should be appreciated, however, that the relative dimensions of the sanitary covering can be such that the handle fills the entire interior thereof—a preferable arrangement since the handle would then be partially grasped by the sides of the plastic member. As will be seen in FIG. 61, discussed below, it may be advantageous to have the sanitary covering as closely encompassed about the handle 145 as possible so that other coverings can be forced over the first covering until no further coverings will fit. At this point, a store employee must remove the stack of coverings to allow a new series of coverings to be applied over the cart handle.

FIG. 49 shows an alternative embodiment of a sanitary covering 149 for the handle 145 of a hand-propelled cart shown in phantom throughout most of the covering. It should be appreciated that the central portion of the covering 149 is the same as that shown in FIGS. 44–48 with the addition of end covering portions 151 which extend over the curved portions of the handle 145. It should also be appreciated that the end covering portions 151 of the sanitary covering do not incorporate the resilient clip arrangement shown in FIGS. 44–48, but comprise openings that fit over the ends of the cart handle 145. Moreover, the end portions 151 are designed to fit over the ends of the handle 145 to shroud the handle and to assume the shape of that particular handle. The shape depicted in FIG. 49 as well as the shapes depicted in some of the figures thereafter are designed to fit over the particular types of handles shown. They are not the only possible shapes.

FIG. 50 is a cross-sectional view of one of the end portions 151 of the sanitary covering 149 in line with the handle 145 of a hand-propelled cart. FIG. 50 shows how the non-gripping lower ends 152 of the end portions 151 extend downwardly and do not resiliently or grippingly contact the sides of the cart handle 145 as such handle extends downwardly. The more inwardly resilient gripping sections 143 of the central portion of the sanitary covering 149 do grip and/or surround the horizontal crosspiece 145a of the handle 145. Of course, if it were desired to have the lower ends 152 of the end portions 151 of the sanitary covering 149 contact the sides of the cart handle 145, such lower ends would be designed to be resiliently urged inwardly so that they would make contact with the sides of the handle.

FIG. 51 is a side view of a sanitary covering 149 similar to the covering depicted in FIGS. 49 and 50 diagrammatically showing printed advertising material 154a, 154b, and 154c applied to the surface of the covering.

FIG. 52 is a side elevation of a further embodiment of the invention in which the sanitary covering for the handle of a hand-propelled cart is formed from a series of individual plastic sections 153, the majority of which have a male interlock section 155 at one end which may be snapped together with a female interconnection opening located at the opposite end. The far end section 153a is provided with only a female interconnection opening.

FIG. 53A shows one of the sections 153 viewed toward the end from which the male interlock section 155 protrudes. Both the sections 153 and the male interlock section 155 are provided with a groove 157 in the bottom and the female interconnection opening 159 which surrounds the handle of a hand-propelled cart.

FIG. 53B shows one of the sections 153 viewed toward the end incorporating the female interlock member comprising a larger orifice 161 that will accept the male interlock section 155, leaving a groove 163 at the bottom through which the handle of a hand-propelled cart, not shown, may be pressed. After the handle has been inserted from the side or bottom into the sections 153, it occupies the female interconnection opening in the sections, having passed through the side walls of such sections including the openings 157 and groove 163. The side walls also snap over the male interlock sections 155 and the cart handle is itself accommodated in the openings 159 and 161 of such sections.

FIG. 54 is a sectional view through a still further embodiment of the invention having the general outline of the sanitary covering 149 shown in FIGS. 49 and 51, but provided on the outside with a series of fairly thin plastic or compacted fiber sheets 165 wrapped about the main body portion and adhered one to another to form a layer of individually separable sheets.

FIG. 55 is an elevation or outside view of the sanitary covering depicted in FIG. 54 showing the outside of the layer of individually separable sheets 165. In the embodiment shown in FIGS. 54 and 55, the sanitary covering 149 is provided with a series of fairly thin sheets 165 wrapped about the main body portion of the sanitary covering in a manner such that each cart user may tear therefrom a sheet which may be discarded after use leaving the top surface of the next adhered sheet exposed and ready for use. In other words, each individual sheet provides a new and substantially sterile hand contact surface.

FIGS. 56 and 57 show, respectively, a sectional side view and a partially broken-away upper view of a further embodiment of the invention in which a series of sanitary covering sheets are wrapped about the handle of a hand-propelled cart, each sheet being effectively attached to the sheet underneath by a layer of releasable adhesive, as also shown in FIGS. 54 and 55. The sheets are provided with a series of differentially cutback portions which, in the aggregate, extend further and farther out to the side along the sheets, from the bottom sheet to the top sheet, providing a series of undercut surfaces which a cart user may grasp to remove the outermost sheet. In FIG. 56, the individual sheets are indicated by the reference numerals 167a, 167b, 167c, etc. In both FIGS. 56 and 57, the cutback portions of the sheets are indicated by the reference numerals 169a, 169b, 169c, etc. Since the cutback portion 169 of each sheet, from the lowest sheet to the highest sheet, extends progressively closer to the nominal edge of the layer of sheets, a cart user may place his/her finger under each sheet and, by exerting upward pressure, withdraw the uppermost sheet. In order to prevent more than one sheet at-a-time from being withdrawn, it is advantageous to have the sheets attached to one another by means of differentially adherent adhesive layers. In other words, the lowest sheet will be adhered to the handle of a hand-propelled cart by a fairly retentive adhesive, while each subsequent sheet will be adhered to its underlying sheet by an adhesive that is progressively less retentive. The differential adhesiveness may be attained by progressive dilution of the adhesive using a suitable diluent or an appropriate filler. The adhesive should be flexible, non-toxic, and non-allergenic so that cart users and children who may teethe on the cart handles will suffer no ill effects from contact therewith.

Thin plastic or paper sanitary coverings for handles of hand-propelled carts could pose a danger to children who teethe or chew on such cart handles. Such children could possibly swallow pieces of the plastic or paper coverings. Therefore, where children may have access to sanitary coverings, such coverings should be of a more substantial character—having added strength and durability such as provided by the coverings shown in FIGS. 44–53.

The embodiment of the invention shown in FIGS. 54–57, while using relatively thin plastic material, can be made suitable for use around children if the adhesive between the sanitary coverings is sufficiently strong and durable to form a substantially monolithic deposit of plastic.

The embodiment of the invention shown in FIGS. 52 and 53, wherein separate sections of plastic coverings are interconnected to provide a unitary covering, is also suitable for use around children as long as the interconnected sections are sufficiently secure so that the children cannot pull off sections small enough to swallow. The sections are, of course, made of a plastic that is impossible to chew in the bulk in which it is supplied.

With regard to the embodiment of the invention shown in FIGS. 44–48, the fact that the plastic is of a quality that is strong enough to allow the sanitary coverings made therefrom to withstand onslaughts by teething children, also makes the coverings more expensive and, consequently, unsuitable for disposal after just one use. There are, however, ways to recycle such coverings including recycling with typical household and industrial plastic items in which such items are collected and then melted together to form a cheap amalgamation of plastic suitable for only non-critical uses. However, rather than mixing the high quality plastic coverings with plastics of lesser quality, it is preferable to recycle the coverings so that the plastic is recycled back into new sanitary coverings. FIG. 58 shows such a recycling scheme in diagrammatic flow-sheet form whereby a dispenser 171 attached to a wall 173 of a commercial establishment dispenses sanitary coverings 175 which may be similar to or the same as the coverings depicted in FIGS. 44–48. These sanitary coverings 175 are snapped over the handles 177 of carts 179 by cart users. After use, store personnel remove the sanitary coverings 175 placing them in a recycling receptacle 181 until there is a sufficient quantity of used coverings to warrant collection by a truck 183. The truck 183 conveys the used sanitary coverings 175 to a plant where they are placed in a furnace 185 and melted to a fluid or semi-fluid which is directed to an extruder 187 that extrudes the molten plastic into new plastic sanitary coverings 175*a*. The new coverings 175*a* are then directed to a warehouse 189 from which they may be delivered by a truck 191 back to the store to be placed in a dispenser 171 for reuse.

Alternatively, the collection truck 183 may deliver the used sanitary coverings to a plant where they are deposited into a sanitizing device 193 to be thoroughly disinfected by re-circulated antiseptic solution or the like before being dried and returned to the warehouse 189 for redelivery to the store to be replaced in a dispenser 171 for reuse. It should be appreciated that the recycling, when done on a large scale, can be quite economical and enables the sanitary coverings to be reused at only a nominal cost per each use. The recycling scheme shown in FIG. 55 is a separate closed-loop system in which the same product is recycled separately from other products so that it is not contaminated with the materials of other products and can be reconstituted to its original form at a relatively low cost. There is provided, therefore, a method of recycling adapted especially to the reuse of plastic sanitary coverings for the handles of hand-propelled carts that can accommodate large quantities of cart handles from a number of different business establishments so that significant economies of scale can be realized.

While a preferred snap-on-type sanitary covering is shown being recycled in FIG. 58, it should be appreciated that any type of sanitary covering can be recycled in a process including disinfecting via a suitable sanitizing operation such as one of those shown in FIG. 58.

FIG. 59 is an isometric view of a variation of the sanitary covering shown in FIG. 44, but including an extra handle 193 attached to the top thereof to allow the covering to be more easily forced over and removed from the cart handle.

FIG. 60 shows a variation of the embodiment of the invention depicted in FIG. 59 in which the handle 193 is covered by a plastic protective shield 195 to protect the handle from contamination. The shield 195 can be easily pierced and removed by a cart user prior to removal of the sanitary covering 141 from the cart handle.

FIG. 61 shows a further embodiment of the invention, which, as explained above, provides a somewhat thinner and more resilient plastic sanitary covering 197 for placement over the handle of a hand-propelled cart in the same manner as the embodiment shown in FIG. 44, but which may also accommodate a series of similar plastic coverings snapped over each prior covering so that the cart handle and previously-applied coverings may, in turn, be covered by new plastic coverings. Such sequential application of sanitary coverings 197 may continue through several cycles before the number of coverings applied to the cart handle dictates that no additional coverings can be applied. At this point, the accumulated coverings are removed and recycled, as shown in FIG. 58.

Figure 65:
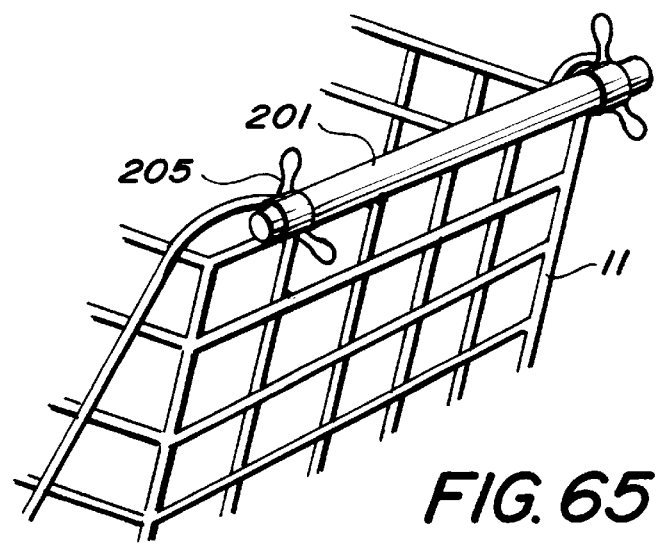
FIG. 65 shows the embodiment of the invention depicted in FIGS. 62 through 64 applied to the handle of a shopping cart.

FIG. 62 is an isometric view of a sanitary covering with an integral clip for temporarily but firmly securing the covering over the handle of a hand-propelled cart. The sanitary covering 201 is formed of plastic in a shape preferably similar to the form shown in FIGS. 44 through 48, but has secured to the ends a heavier metal or plastic loop 203 which surrounds the sanitary covering 201 and is attached thereto. The loop 203 may be biased open by extension arms 205 which are attached to the base by small loops 207 in the bottom of the loop 203 in a manner similar to the arrangement of a well known office clip used for securing papers together. The small loops 207 are better shown in FIG. 63. It will be understood that while only one end of the sanitary covering 201 is shown in FIG. 62 the other end will incorporate a similar outer loop 203 and extension arms 205. When it is wished to open the sanitary covering 201 to place it over the handle of a shopping cart or the like, the extension arms 205 are pressed toward each other causing the entire sanitary covering and integral clips to open, whereupon it can be placed over the handle of the shopping cart and allowed to spring shut again. FIGS. 63 and 64 show two further views of the arrangement shown in FIG. 62, namely a side view in FIG. 63 and an end view in FIG. 64. FIG. 65 shows the sanitary covering 201 shown in FIGS. 62 through 64 in place on a shopping cart handle of a shopping cart 11.

Figure 67:
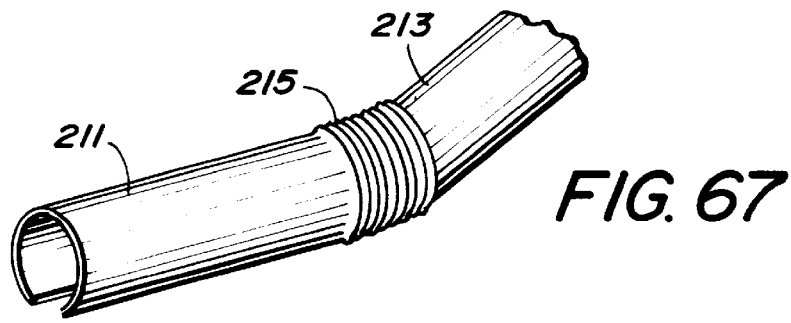
FIG. 67 shows one of the corrugated connecting sections of FIG. 66 in a bent position.
Figure 66:
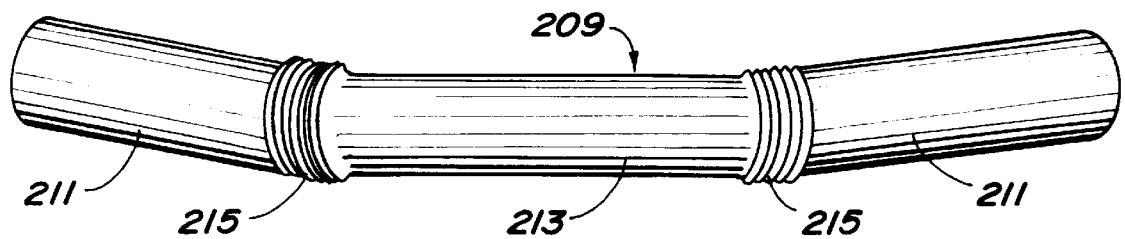
FIG. 66 shows an alternative embodiment of the invention in which end portions of the sanitary wrapping are attached or connected to the central portion by flexible corrugated sections.

FIG. 66 shows an improved sanitary covering for a shopping cart in which the central portion of the covering 209 which extends about the shopping cart handle when in operative position has two similarly constructed end portions 211 adapted to cover the supports for the shopping cart handle. Such end portions 211 are connected to the central portion 213 of the covering by corrugated plastic sections 215 integral with the end positions 211 and central portion 213. The corrugated sections 215, which are similar in form to the bellows of an accordion, are readily bent or adjusted to allow the ends of the sanitary wrapping to be bent into any position to allow such end sections 211 to be aligned with and passed over the supports for the cart handle. A more bent or inclined position of one of the ends is shown in FIG. 67. The use of the embodiment of the invention shown in FIGS. 66 and 67 on an actual shopping cart 11 is shown in FIG. 68.

Figure 69:
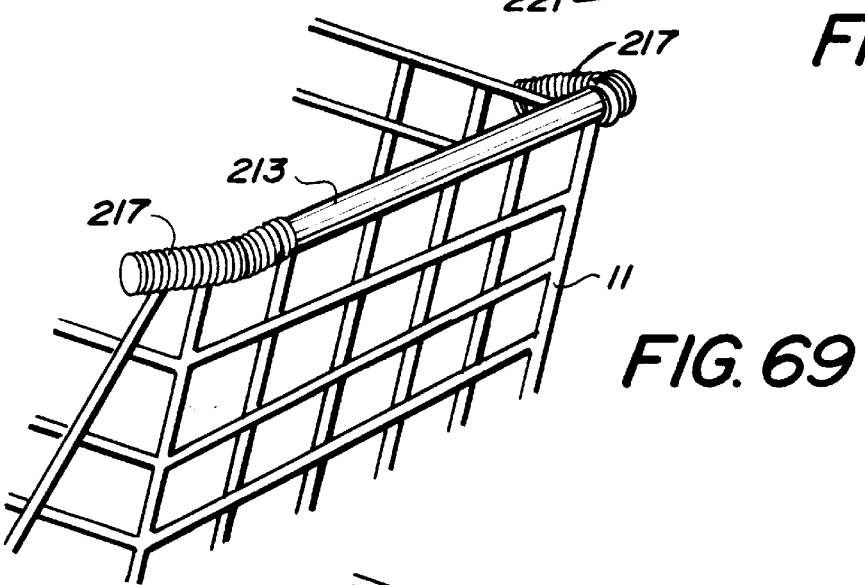
FIG. 69 shows an isometric view similar to that shown in FIG. 68, but wherein the entire end portion of the sanitary wrapping is corrugated.
Figure 68:
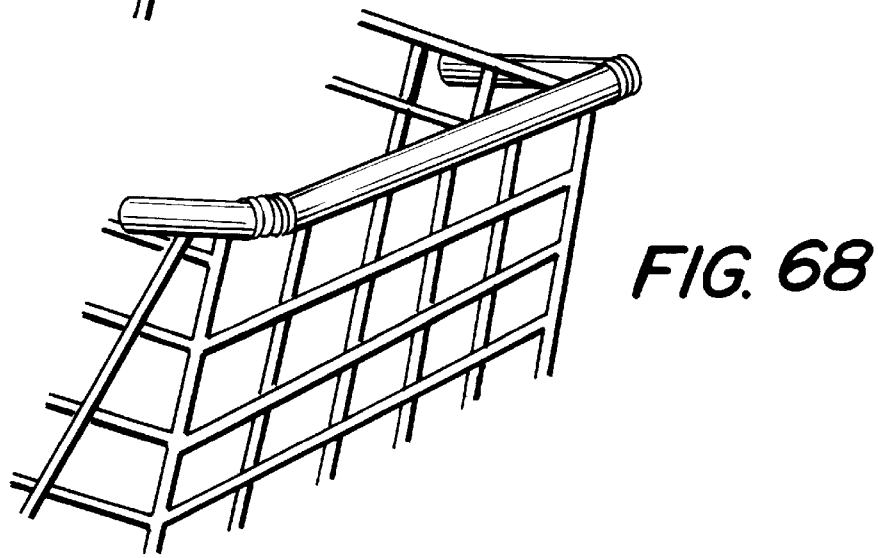
FIG. 68 shows the use of the embodiment of FIGS. 66 and 67 in use on a shopping cart.

An alternative embodiment of the invention shown in FIGS. 66 through 68 in which the ends of the sanitary covering or wrapping of the invention are completely corrugated allowing additional adjustability is shown in FIG. 69 where two completely corrugated sections 217 are shown attached to the ends of a central hollow tubular section 213. The arrangement shown makes the sanitary covering or wrapping of the invention even more adaptable to various sizes and shapes of carts, particularly since the center section can be made shorter than is likely to be met with in most cart handles and the flexibility of the corrugated end sections allows them to adjust to wherever the ends of the handle occur, at which point the bend in the corrugated sections occur. The bellows form of the corrugation enables them to readily adapt to various configurations of handles and handle supports.

Figure 70:
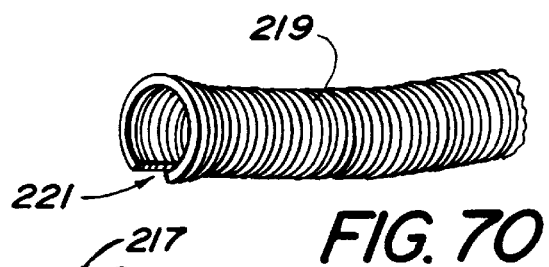
FIG. 70 shows an enlarged section of corrugated ends of the embodiment of the invention shown in FIG. 69.

FIG. 70 shows an enlarged isometric view of one of the corrugated end portions of the embodiment of the invention shown in FIG. 69 showing the end of the sanitary plastic wrapping or covering comprised in accordance with the invention of a corrugated plastic tube 219 having a slot 221 in one side through which the handle or other associated parts of the shopping car may be inserted.

Figure 71:
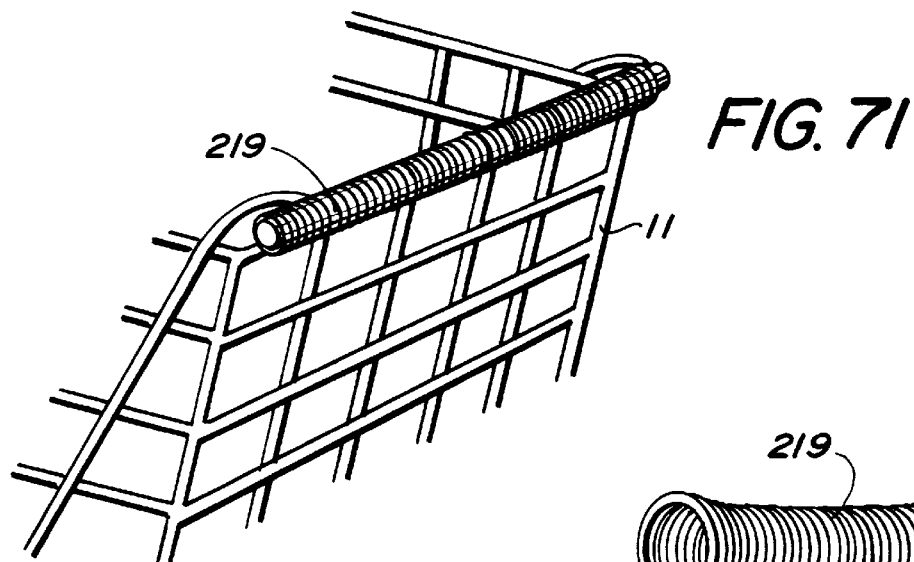
FIG. 71 shows an alternative embodiment of the invention applied to the handle of a shopping cart in which the entire sanitary covering comprises a plurality of folds like the bellows of an accordion.

FIG. 71 shows an embodiment of the invention similar to that shown in FIG. 70, but in which substantially the entire sanitary covering or wrapping is comprised of a corrugated construction applied over the handles of a shopping cart. In this case the covering is only long enough to cover the handle itself, but could also be longer in which case the ends could cover other portions of the shopping cart as shown in FIG. 69.

Figure 72:
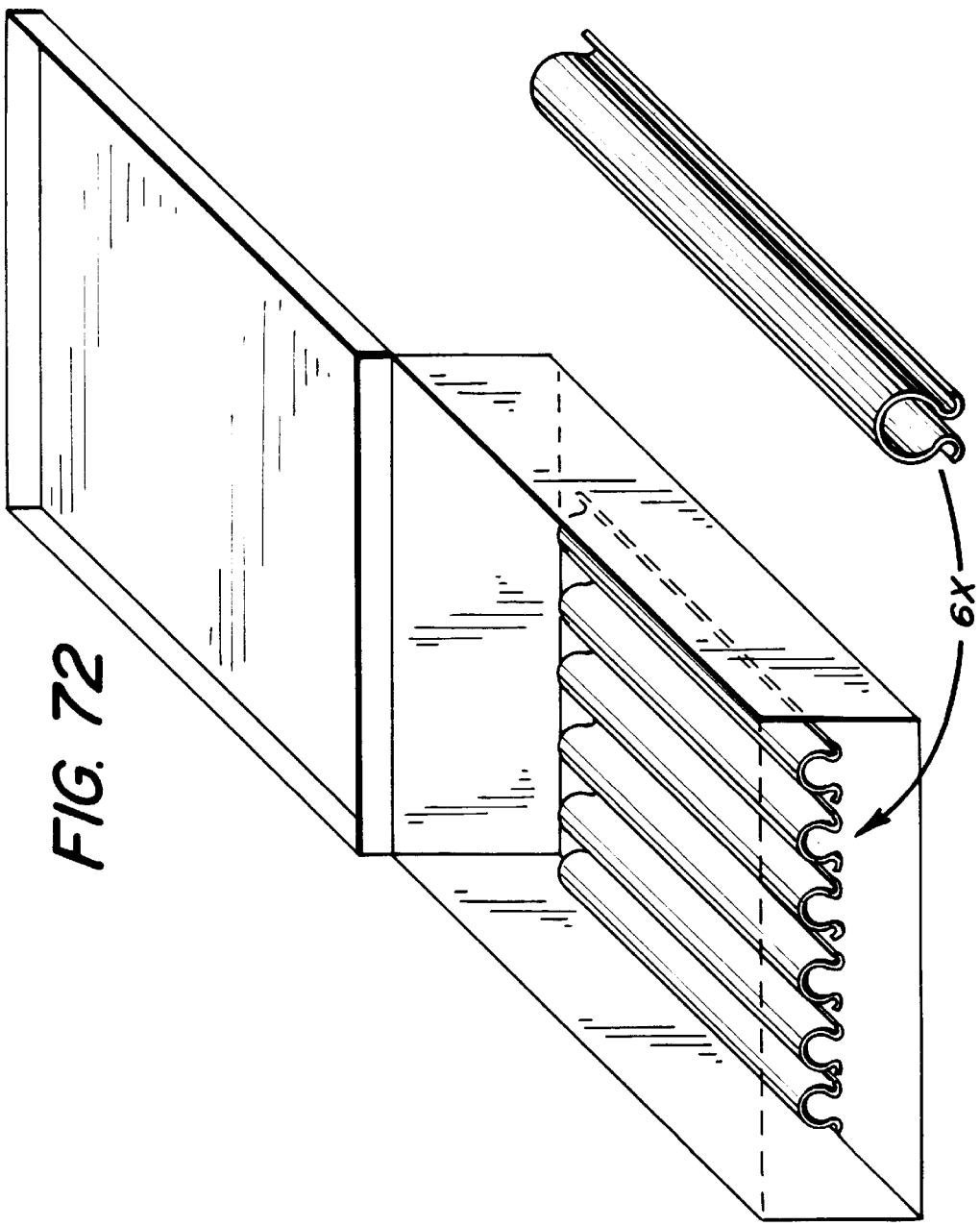
FIG. 72 shows several sanitary coverings such as shown in FIGS. 44 through 48 arranged in a box.

FIG. 72 shows a series of closed crescent shaped coverings 141 such as shown in FIGS. 44 through 48 placed in a container or box 223. The sanitary wrappings or coverings are placed in the container 223 which has a lid 225 in such an arrangement that they can be easily removed by a potential user and snapped over the handle of a shopping cart, not shown. Alternatively the sanitary coverings can be easily fed into a dispenser such as shown in FIG. 58. An isometric view of one of the sanitary coverings 141 slightly enlarged is shown to the side of the container 223 to illustrate how the sanitary covering can be withdrawn from the container ready for use.

In FIG. 58, a recycling of sanitary coverings has been shown in which the coverings 175 are either remelted after use or washed with disinfectant and then reused. The melted plastic in the case where the plastic covering is remelted is preferably re-extruded into the form of additional substantially identical sanitary wrappings and in that way recycled. In either case, there is essentially a full recycling of either a reformed or a sanitized or washed sanitary covering back to use allowing a full cycle recycling operation. It will be understood, however, that in some cases when the coverings are melted, that the plastic may, instead of being fully recycled back to the original use, be used to form other products and new, or virgin, plastic used in the sanitary covers during their production by extrusion or the like. In another variation, the clip arrangement shown in FIGS. 62 through 65 could be applied to other forms of sanitary covering such as that shown in FIGS. 38 through 43.

There have been described above, in connection with the present invention, a number of different embodiments of sanitary coverings for isolating potentially contaminated handles of hand-propelled carts from the hands of cart users in order to prevent the transfer of infectious agents from one cart user to another. While the present invention has been described at some length, it is not intended that it should be limited to any such embodiments or any particular embodiment, but is to be construed broadly with reference to the appended claims so as to provide the broadest possible interpretation of such claims in view of the prior art and, therefore, to effectively encompass the intended scope of the invention.

I claim:

1. A portable sanitary shielding means for preventing contact contamination of the human body as the result of direct contact with the handle of a hand-propelled cart comprising:

(a) a flexible sheet of substantially biologically impervious material having a length coextensive with that of a hand contact portion of a cart handle and a width such that the sheet, upon wrapping completely about the cart handle, has an overlap of material sufficient to completely encapsulate the handle to form an encapsulating hand contact shield member, (b) resilient clip-type means integrally secured to said sheet at opposite ends of the flexible sheet for resiliently securing the sheet about the cart handle.

2. A sanitary shielding means according to claim 1 further comprising a flexible material pouch attached to one side of the flexible sheet in a position to depend therefrom between the resilient clip-type means when such means are secured about the handle of a hand-propelled cart, the pouch having a size such that the sheet material forming the encapsulating hand contact shield member together with the clip-type means can be folded and inserted into the pouch when not in use.

3. A sanitary shielding means for preventing contact contamination of the human body as the result of direct contact with the handle of a hand-propelled cart comprising:

(a) a plurality of resilient plastic members having elongated arcuate configurations with hollow interiors, resilient lips defining openings smaller than the diameter of the cart handle, the resilient lips having inwardly inclined lower surfaces adapted to contact the sides of the cart handle to facilitate forced movement of the lower surfaces outwardly and over the handle, and (b) flexible interconnection means for flexibly joining said resilient members to form a continuous sanitary shielding means.

4. A sanitary shielding means for preventing contact contamination of the human body as the result of direct contact with the handle of a hand-propelled cart comprising:

(a) a resilient plastic member having an elongated arcuate configuration with a hollow interior and resilient lips extending along the length of the resilient plastic member defining an opening smaller than the diameter of the cart handle, the resilient lips having inwardly inclined surfaces along the opening adapted to contact the sides of the cart handle and to facilitate forced movement of the inclined surfaces outwardly and over the handle, (b) flexible end sections integrally attached to the resilient plastic member having a plurality of folds arranged and constructed to cover any further outer end sections of the cart handle.

5. A sanitary shielding means for sanitizing a hand-propelled cart handle comprising:
   (a) a resilient plastic member having a length sufficient to completely encapsulate a handle of a hand-propelled cart,
   (b) said resilient plastic member having a narrow opening along one side from end to end having a width sufficient to allow a portion of the side of the cart handle to partially intrude into said opening,
   (c) outwardly inclined lip portions extending along the narrow opening having inclined inner and outer surfaces arranged along the opening at such angle as to tend to bias the lips of the opening farther apart when the cart handle is forcibly pressed against the side of the inclined outer surfaces from the outside and against the inclined inner surfaces from the inside of the sanitary covering,
   (d) the resilience of the resilient plastic member being such that an average person using the hand-propelled cart will be able upon pressing the inclined surfaces and cart oppositely relative to each other, to force the cart handle between the lips, as well as being sufficient to securely retain the resilient plastic member upon the cart handle when only the force necessary to maneuver the cart by hand contact upon the handle is used, and
   (e) end shield members for extending over the handle support sections of the hand-held cart wherein said end shield sections are comprised at least in part of a plurality of flexible folds.

6. A sanitary shielding means in accordance with claim 5 wherein at least a portion of the resilient plastic member and end shield members taken together are formed of flexible folds with a groove in the side to enable placement over the handle and handle supports.

7. A sanitary shielding means for preventing contact contamination of the human body as the result of direct contact with the handle of a hand-propelled cart comprising an elongated resilient plastic member, the member having a hollow interior, a cross-sectional profile having an arcuate shape with a terminal pair of outwardly inclined lips, and a length substantially coincident with the length of the straight portion of the cart handle, the lips being resilient and defining an opening smaller than the diameter of the cart handle along the entire length of the elongated resilient plastic member, the resilient lips being adapted to contact the sides of the cart handle and to facilitate forced movement of the lips outwardly and over the handle when placing the elongated plastic member upon a cart handle and wherein the elongated resilient plastic member is comprised of a plurality of flexible folds.

8. A portable sanitary shielding means for preventing contact contamination of the human body as the result of direct contact with the handle of a hand-propelled cart comprising:
   (a) an elongated resilient plastic member having a hollow interior nominally slightly smaller in diameter than the exterior diameter of a cart handle for which shielding is intended to be provided and a length nominally about the same to somewhat longer than such handle,
   (b) said elongated resilient plastic member having an elongated opening along one side to allow placement of said elongated resilient member over the cart handle,
   (c) at least partially flexible end shields extending from the ends of said elongated resilient plastic member and having an opening in one side for placement of the end shields over mounting or support portions of the handle of the cart in a manner to shield the human body from contact with said mounting or support portions,
   (d) at least a portion of at least one of the elongated resilient plastic member, the flexible end shields and the interconnection between the flexible end shields and the elongated resilient plastic member being transversely corrugated to render them relatively easily flexible in a longitudinal direction.

9. A portable sanitary shielding means in accordance with claim 8 wherein the interconnections between the flexible end shields and the elongated resilient plastic member are corrugated to provide flexibility and adjustability.

10. A portable sanitary shielding means in accordance with claim 9 wherein the flexible end shields are corrugated to provide flexibility and adjustability.

11. A portable sanitary shielding means in accordance with claim 10 wherein the elongated resilient plastic member is corrugated to provide flexibility and adjustability.

12. A portable sanitary shielding means for preventing contact contamination of the human body as a result of direct contact with the handle of a hand-propelled cart comprising:
   (a) an elongated resilient plastic member having a hollow interior nominally slightly smaller in diameter than the exterior diameter of a cart handle for which shielding is intended and a length nominally about the same to somewhat longer than such handle,
   (b) an elongated opening along one side of said elongated resilient plastic member to allow placement of said elongated resilient member over the cart handle,
   (c) at least a portion of said elongated resilient plastic member hang a corrugated construction including transverse corrugations of the elongated plastic construction to provide flexibility and adjustability.

* * * * *